United States Patent [19]
Orvig et al.

[11] Patent Number: 6,060,614
[45] Date of Patent: May 9, 2000

[54] CHELATING LIGANDS HAVING A TRIPODAL BACKBONE

[75] Inventors: Chris Orvig, Vancouver, Canada; Mark P. Lowe, Pontefract, United Kingdom

[73] Assignee: The University of British Columbia, Vancouver, Canada

[21] Appl. No.: 09/112,944

[22] Filed: Jul. 10, 1998

Related U.S. Application Data

[60] Provisional application No. 60/052,203, Jul. 10, 1997.

[51] Int. Cl.$^7$ .................................. C07F 5/00; C07F 9/02
[52] U.S. Cl. ................................ 556/13; 556/1; 556/174; 564/15; 534/15
[58] Field of Search .................................. 564/15; 556/1, 556/13, 174; 534/15

[56] References Cited

U.S. PATENT DOCUMENTS

| | | | |
|---|---|---|---|
| 4,999,443 | 3/1991 | Bertleff et al. | 556/136 |
| 5,405,601 | 4/1995 | Dunn et al. | 424/9 |
| 5,565,184 | 10/1996 | Dunn et al. | 424/1.65 |

OTHER PUBLICATIONS

Mark P. Lowe, et al., "Highly Symmetric Group 13 Metal–Phosphinato Complexes: Multinuclear NMR ($^{27}$Al, $^{31}$P, $^{71}$Ga) Determination of Stability Constants at Low pH", J. Am. Chem. Soc. 1996, 118, 10446–10456.

P. Caravan, et al., "Selectivity among, and aggregation of, lanthanide ions", Journal of Alloys and Compounds 000 (1996) 000–000.

Lowe, M.P. et al., "Tightening the Hydrophobic Belt: Effects of Backbone and Donor Group Variation on Podand Ligand Complexes of the Lanthanides", Inorg. Chem. 1998, 37, 1637–1647.

Primary Examiner—Porfirio Nazario-Gonzalez
Attorney, Agent, or Firm—Oyen Wiggs Green & Mutala

[57] ABSTRACT

The invention relates to novel chelating ligands which incorporate a tripodal backbone. More particularly, the invention pertains to novel tripodal ligands which form coordination compounds with a variety of metal ions, particularly, but not exclusively, trivalent metal ions and lanthanide metal ions, which are useful in nuclear medicine. A novel amine phosphinate tripodal ligand, a chelating ligand and a process therefor involving a metal ion and particularly a trivalent metal ion of the group 13 metals and the rare earths. The process comprises complexing Tc or Re or any one of the group 13 metals, Al, Ga and In, and any one of the rare earths, Sc, Y, La, Ce, Pr, Nd, Pm, Sm, Eu, Gd, Th, Dy, Ho, En, Tm, Yb and Lu, with an amine phosphinate tripodal ligand.

22 Claims, 8 Drawing Sheets

CHELATING LIGANDS HAVING A TRIPODAL BACKBONE

This non-provisional application under 35 U.S.C. 119(e) claims the benefit of provisional application Ser. No. 60/052,203, filed Jul. 10, 1997.

FIELD OF THE INVENTION

The invention relates to novel chelating ligands which incorporate a tripodal backbone. More particularly, the invention pertains to novel tripodal ligands which form coordination compounds with a variety of metal ions, particularly, but not exclusively, trivalent metal ions of the group 13 metals and lanthanide metal ions, which are useful in nuclear medicine.

BACKGROUND OF THE INVENTION

In recent years, vigorous research activity has been conducted to identify and synthesize suitable chelating agents for metal ions and particularly trivalent metal ions such as the group 13 metals and the lanthanides, for use in nuclear medicine. This is because of the deleterious effects of these metals (e.g. concern over aluminum neurotoxicity) and their burgeoning use in vivo as diagnostic probes. For example, gallium and indium radionuclides are used in radiopharmaceuticals. Further, the physical properties of the lanthanides are exploited as luminescent, EPR, and NMR shift probes. They also have widespread application as magnetic resonance imaging contrast agents. Similarities in oxophilicity (e.g. Al(III), Ln(III) and ionic radii (e.g. In(III), Ln(III) do not necessarily result in a complementary chemistry for the respective group 13 and lanthanide ions.

The following three patents disclose transition metal complexes and functionalized tripodal ligands for imaging applications:

| U.S. Pat. No. | Inventor | Issue Date |
| --- | --- | --- |
| 4,999,443 | Bertleff et al. | March 12, 1991 |
| 5,405,601 | Dunn et al. | April 11, 1995 |
| 5,565,184 | Dunn et al. | October 15, 1996 |

SUMMARY OF THE INVENTION

The invention relates to novel compositions of matter, a process for preparing these novel compositions of matter, a new series of chelating ligands, and a series of their metal complexes, which have use in diagnostic and therapeutic nuclear medicine.

The invention is directed to an amine phosphinate tripodal ligand of the formula:

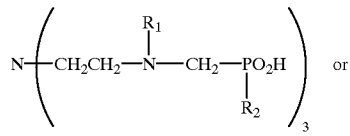 or

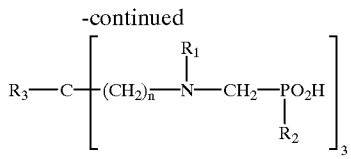

wherein n is 1 or 2, $R_1$ and $R_3$ are H, $CH_3$, $C_2H_5$ or other alkyl; and $R_2$ is $C_6H_5$, $CH_3$, $CH_2OH$, other alkyl, substituted alkyl, or aryl, and physiologically compatible salts and derivatives thereof.

The amine phosphinate tripodal ligand can be:

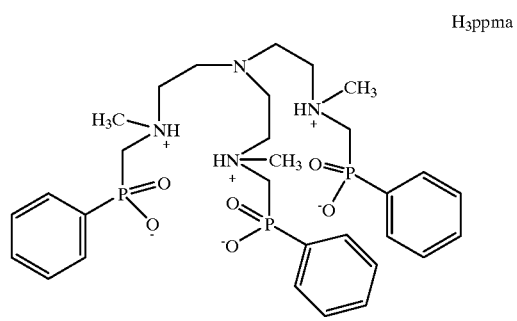

$H_3ppma$

The invention is also directed to a process of preparing an amine phosphinate tripodal ligand of the formula:

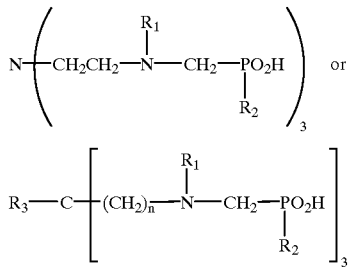

wherein n is 1 or 2, $R_1$ and $R_3$ are H, $CH_3$, $C_2H_5$ or other alkyl; and $R_2$ is $C_6H_5$, $CH_3$, $CH_2OH$, other alkyl, substituted alkyl, or aryl, and physiologically compatible salts and derivatives thereof, which comprises (a) reacting a tripodal amine of the formula:

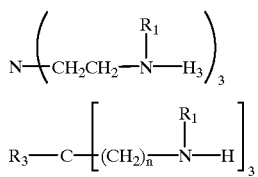

wherein n is 1 or 2, $R_1$ and $R_3$ are H, $CH_3$, $C_2H_5$, or other alkyl; with $H_2P(R_2)O_2$ and $CH_2O$ or $(CH_2O)_m$, wherein $R_2$ is H, $C_6H_5$, $CH_3$, other alkyl, substituted alkyl, or aryl, and m is 2 or greater; or (b) converting the $R_2$ group of one amine phosphinate tripodal ligand to another $R_2$ group by using formaldehyde or paraformaldehyde.

The invention is also directed to a process of preparing an amine phosphinate tripodal ligand of the formula:

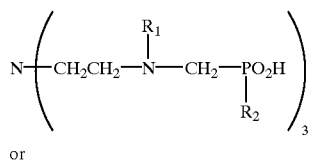

or

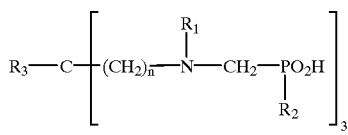

wherein n is 1 or 2, $R_1$ and $R_3$ are H, $CH_3$, $C_2H_5$ or other alkyl; and $R_2$ is $CH_2OH$, and physiologically compatible salts and derivatives thereof, which comprises converting an amine phosphinate tripodal ligand wherein $R_2$ is H to an amine phosphinate tripodal ligand wherein $R_2$ is $CH_2OH$ by reacting with formaldehyde or paraformaldehyde.

The invention is also directed to a process of chelating a metal ion with an aminephosphinate tripodal ligand. The invention is also directed to a process of chelating a trivalent metal ion such as Technetium (Tc) or Rhenium (Re) or a trivalent metal ion of the group 13 metals and the rare earths which comprise complexing any one of the group 13 metals, Al, Ga and In, and any one of the rare earths or lanthanides, Sc, Y, La, Ce, Pr, Nd, Pm, Sm, Eu, Gd, Tb, Dy, Ho, Er, Tm, Yb and Lu, with the amine phosphinate tripodal ligand.

In the process of the invention, any one of the group 13 metals, Al, Ga and In can be complexed with the amine phosphinate tripodal ligand or any one of the rare earth metals, Sc, Y, La, Ce, Pr, Nd, Pm, Sm, Eu, Gd, Tb, Dy, Ho, Er, Tm, Yb and Lu, can be complexed with the amine phosphinate tripodal ligand. The invention also includes the chelation of Beta emitting radioactive isotopes as therapeutic agents, including but not limited to the isotopes Sm 153, Ho 166, Y 90, Pm 149, Pr 145, Dy 166, Ln 177 and Yb, and for imaging applications including but not limited to In 111.

In one form, the amine phosphinate tripodal ligand can have the following formula:

H$_3$ppma

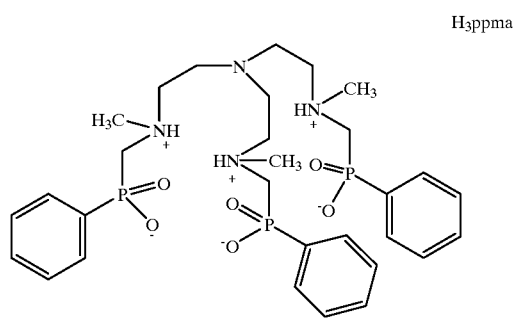

The invention is also directed to a chelate comprising a complex of a metal ion or a trivalent metal ion such as Tc or Re or a trivalent metal ion of the group 13 metals, Al, Ga and In, and the rare earths, Sc, Y, La, Ce, Pr, Nd, Pm, Sm, Eu, Gd, Tb, Dy, Ho, Er, Tm, Yb and Lu and the amine phosphinate tripodal ligand. The complex can be a group 13 metal complex and the metal can be selected from the group consisting of Al, Ga and In or the complex can be a rare earth complex, including Sc and Y, and the lanthanide can be selected from the group consisting of La, Ce, Pr, Nd, Pm, Sm, Eu, Gd, Tb, Dy, Ho, Er, Tm, Yb and Lu.

BRIEF DESCRIPTION OF DRAWINGS

In drawings which illustrate specific embodiments of the invention, but which should not be construed as restricting the spirit or scope of the invention in any way.

DETAILED DESCRIPTION OF THE INVENTION

Figure 1:
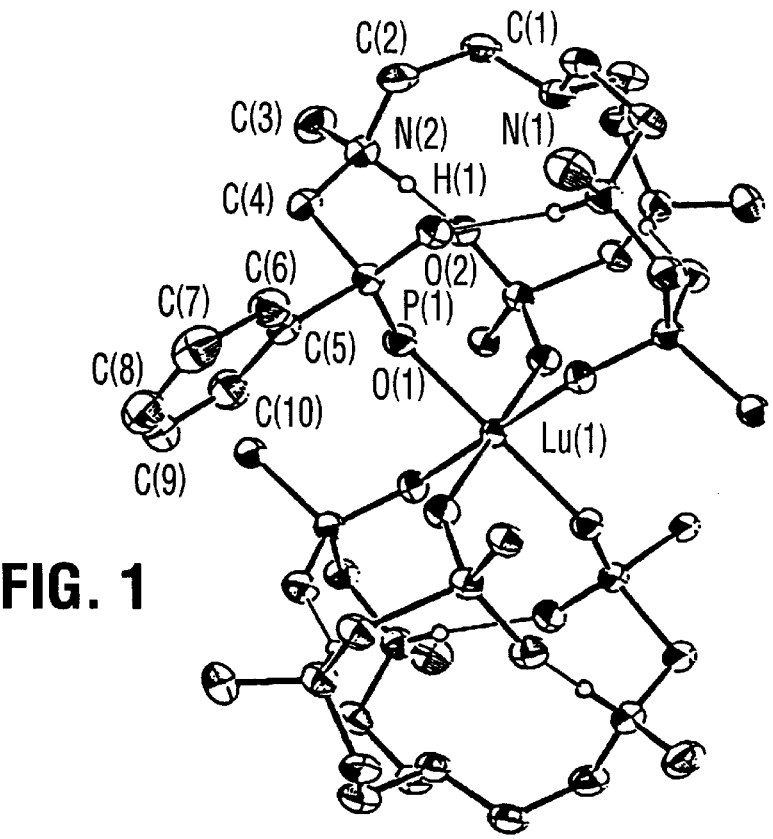
FIG. 1 depicts an ORTEP representation of the cation in [Lu(H$_3$ppma)$_2$](NO$_3$)$_3$.3H$_2$O (25% probability thermal ellipsoids). Only one phenyl group is shown for clarity.

An N$_4$O$_3$ tripodal tren-based (aminomethylene) phosphinato ligand tris(4-(phenylphosphinato)-3-methyl-3-azabutyl)amine (H$_3$ppma) has been synthesized, and its complexation properties with the group 13 metals Al, Ga, and In have been investigated. The molecular structure of the indium complex [In(H$_3$ppma)$_2$](NO$_3$)$_3$.3H$_2$O (C$_{60}$H$_{96}$-InN$_{11}$O$_{24}$P$_6$) has been solved by X-ray methods; the complex crystallizes in the trigonal space group R3c, with a=18.984(3) Å, c=36.256(5) Å, and Z=6. The structure was solved by Patterson methods and was refined by full-matrix least-squares procedures to R=0.040 (R$_w$=0.039) for 1415 reflections with I>3σ(I). The structure of the bis-complex showed the ligand to coordinate in a tridentate manner through the three phosphinate oxygens, resulting in a bicapped octahedral structure of exact $S_6$ symmetry. The solved structure was of the RRRSSS diastereomer, where half of the molecule contained phosphorus atoms of R chirality and the other half contained phosphorus atoms of S chirality. The highly symmetric environment about the metal atoms produces a low electric field gradient at the metal nucleus leading to unusually narrow line widths in the $^{27}$Al, $^{71}$Ga, and $^{115}$In NMR spectra. The aluminum complex [Al(H$_3$ppma)$_2$](NO$_3$)$_3$.2H$_2$O exhibited an extremely rare example of aluminum-phosphorus coupling ion both the $^{31}$P and $^{27}$Al NMR spectra, where $^2J_{AlP}$ was shown from both spectra to be 6.7 Hz. The narrow line widths made the complexes amenable to stability constant studies via a combination of $^{27}$Al, $^{71}$Ga, and 31P NMR spectroscopies (25° C.). The formation constants for In$^{3+}$ (log $\beta_{2 \geq 5,4}$), Ga$^{3+}$ (log $\beta_2$=4.24), and Al$^{3+}$ (log $\beta_1$=0.93, log $\beta_2$=3.45) decrease by an order of magnitude as the group is ascended, consistent with increasing steric interactions of the phenyl groups as the two trisphosphinate ligands are crowded together in order to coordinate the smaller metal ions. Variable temperature $^{27}$Al and $^{31}$P NMR spectroscopic studies indicated the RRRSSS diastereomer to be rigid up to 55° C. in CD$_3$OD.

The results of this work were published in J. Am. Chem. Soc. 1996, 118, 10446–10456, under the title "Highly Symmetric Group 13 Metal-Phosphinato Complexes: Multinuclear NMR ($^{27}$Al, $^{31}$P, $^{71}$Ga) Determination of Stability Constants at Low pH", Mark P. Lowe, Steven J. Rettig, and Chris Orvig. The full disclosure in this article is incorporated in the specification herein by reference.

General Synthetic Procedure. The appropriate tripodal amine (derivatives of tren and tame specifically) are reacted with a suitable phosphinic acid and formaldehyde under Moedritzer-Irani synthesis (Moedritzer, K., Irani, R. R., *J. Org. Chem.* 1966, 31, 1603) conditions as shown below for H$_3$pma and H$_3$ppma. The P-H derivatives such as H$_3$pma can then be used to make further derivatives as is shown below for H$_3$hpma.

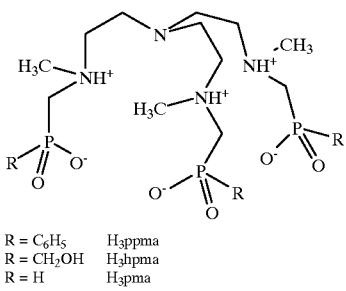

R = C$_6$H$_5$   H$_3$ppma
R = CH$_2$OH   H$_3$hpma
R = H       H$_3$pma

EXAMPLES

Tris(4-phosphinato-3-methyl-3-azabutyl)amine (H$_3$pma). A stirred solution of tris(3-methyl-3-azabutyl)amine (0.50 g, 2.66 mmol) and 50% H$_3$PO$_2$ (1.40 g, 10.61 mmol) in H$_2$O (7 mL) was heated to 40° C. This amine was synthesized by the reaction of tren with ethylchloroformate followed by the reduction of the resulting carbamate with lithium aluminum hydride to give the tri-N-methylated amine: Schmidt, H., Lensink, C., Xi, S. K., Verkade, J. G. *Z. Anorg. Allg. Chem.* 1989, 578, 75. Paraformaldehyde (0.32 g, 10.67 mmol) was slowly added over 1 hr. The reaction was heated for a further 4 hours and then the solvent removed to yield a colorless oil. The oil was taken up in H$_2$O (10 mL), loaded onto an anion exchange column (Amberlite IRA 412) and eluted with water to remove any unreacted H$_3$PO$_2$ or biproduct (HOCH$_2$PH(O)OH). On removal of the solvent, a colorless oil was obtained of H$_3$pma.2HCl.4H$_2$O. Yield=1.21 g (78%). $^1$H NMR (200 MHz, D$_2$O) pD=6.83: δ2.96 (t, 6H, ethylenic CH$_2$ $^3J_{HH}$=6.6 Hz), 3.30 (t, 6H, ethylenic CH$_2$, $^3J_{HH}$=6.6 Hz), 2.85 (s, 9H, methyl NCH$_3$), 3.14 (d, 6H, methylenic NCH$_2$P, $^2J$=10.5 Hz), 7.17 (d, 3H, phosphinic PH, $^3J_{PH}$=540.4 Hz). $^{31}$P{H} (80 MHz, D$_2$O) pD=6.83: δ12.45.

Tris(4-phenylphosphinato-3-methyl-3-azabutyl)amine trihydrochloride monohydrate (H$_3$ppma.3HCl.H$_2$O). Phenylphosphinic acid (2.13 g, 14.99 mmol) and tris(3-azabutyl)amine (0.91 g, 4.83 mmol) were dissolved in distilled water (20 mL). After slow addition of 37% HCl (20 mL), the temperature of the stirred solution was raised to reflux (≈110° C.) and 37% w/w aqueous formaldehyde (2.44 g, 30.09 mmol) was added dropwise over a period of 30 min. The reaction was refluxed for a further 5 hours, after which time the HCl—water solvent mixture was concentrated under vacuum almost to dryness. The resulting syrup was taken up in ethanol (100 mL), and acetone (900 mL) was added to give a cloudy solution which was cooled, then filtered. A white highly hygroscopic powder was obtained; this was taken up in water and the solvent removed once more. Drying under vacuum for 12 hours gave a glassy, slightly hygroscopic solid to yield 2.40 g (64%); Anal. Calcd (found) for C$_{30}$H$_{45}$N$_4$O$_6$P$_3$.3HCl.H$_2$O: C, 46.31 (46.58); H, 6.48 (6.48): N, 7.20 (7.31). Potentiometric studies were consistent with this molecular weight. Mass spectrum (+LSIMS):m/z=651 ([L+1]$^+$,[C$_{30}$H$_{46}$N$_4$O$_6$P$_3$]$^+$). IR (cm$^{-1}$, KBr disk): 3410, 2460 (b s, $_{N-H}$, $_{O-H}$), 1645 (w, $_{N-H}$), 1438 (s, $_{P-Ph}$), 1206, 1131, 957 ($_{P-O}$), 740, 685, 599 ($_{P-C}$, $_{P-Ph}$). UV ($_{max}$, nm (,M$^{-1}$cm$^{-1}$)): pH=1.5, 258 (1375), 264 (1833), 271 (1512).

Tris(4-hydroxymethylenephosphinato-3-methyl-3-azabutyl)amine(H$_3$hpma).

A stirred solution of H$_3$pma.2HCl.4H$_2$O (0.22 g, 0.28 mmol) in 6M HCl (20 mL) was heated to reflux. Aqueous 37% formaldehyde (0.25 g. 3.08 mmol) was slowly added over 1 hour. The reaction was heated at reflux overnight and then the solvent removed under vacuum to yield a colorless oil. The oil was taken up in H$_2$O (10 mL), loaded onto an anion exchange column (Amberlite IRA 412) and eluted with water. On removal of the solvent, a colorless oil was obtained of H$_3$hpma.4HCl.7H$_2$O. 0.387 g was obtained, but there was a lot of HCl and H$_2$O still present. Potentiometry indicated that 0.387 g contained 0.48 mmol of ligand, therefore Mw=792.12. Mw without HCl or water is 512.42, which leaves an extra 283.41. Potentiometry gives the excess acid as about 4 HCl which means about 7 waters. An alternative method is to do the H$_3$pma reactions as before and then carry on with more paraformaldehyde at 100° C. in same solution, i.e. avoid the HCl treatment. After passing through anion exchange, there is 0.3HCl (from column) and one water c.f. H$_3$ppma, H$_3$pma. $^1$H NMR (200 MHz, D$_2$O) pD=7.03: δ 3.00 (t, 6H, ethylenic CH$_2$), 3.41 (t, 6H, ethylenic CH$_2$), 2.94 (s, 9H, methyl NCH$_3$), 3.30 (d, 6H, methylenic NCH$_2$P, $^2J_{PH}$=8.54 Hz), 3.68 (d, 6H, hydroxymethylene HOCH$_2$P, $^2J_{PH}$=6.35 Hz). $^{31}$P{H} (80 MHz, D$_2$O) pD=7.03: δ27.35.

Figure 12:
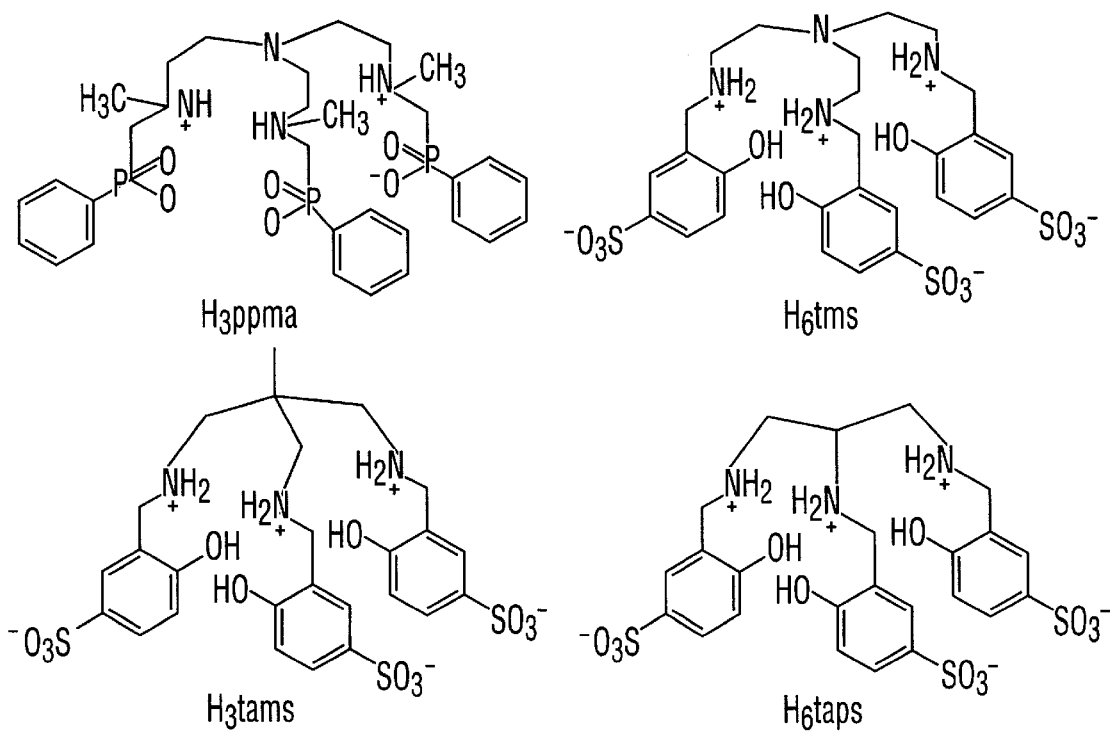
FIG. 12 illustrates the graphical formulae for H$_3$ppma, H$_6$trns, H$_6$tams and H$_6$taps.

Recent investigation[1] of the inventors has focused on the chelation of metal ions and trivalent metal ions such as Tc and Re and the group 13 metals and the lanthanides with a variety of mixed nitrogen/oxygen donors in amine phosphinate tripodal ligands. However, until the water soluble sulphonated analogs were synthesized[2,3] little was known of the solution behavior. The coordination mode of the ligand can be metal dependent. For instance, in aqueous solution $H_6$trns (see FIG. 12) forms bicapped bis(ligand) lanthanide complexes in which bonding is solely through the phenolic oxygens,[7] whereas the Ga(III) and In(III) form 1:1 encapsulated complexes in which bonding occurs with both oxygen and nitrogen donors, while Al(III) does not form a stable complex with $H_6$trns in aqueous solution. 25 The capped and bicapped lanthanide complexes of $H_6$trns have 16 membered chelate rings, much larger than the 5 and 6 membered rings in the encapsulated complexes. It has been suggested[7] that there is an effect which predisposes the ligand to a binding posture, for example the inter and intrastrand hydrogen bonding between protonated nitrogens and phenolic oxygens. The hydrogen bonding, coupled with the large chelate ring size, can result in a ligand which suffers little or no strain energy in accommodating different sized lanthanide ions, and thus the changes in stability noted (an unprecedented 5 orders of magnitude increase in stability from Nd—Yb) correlated with the increasing effective nuclear charge.[7]

Figure 13:
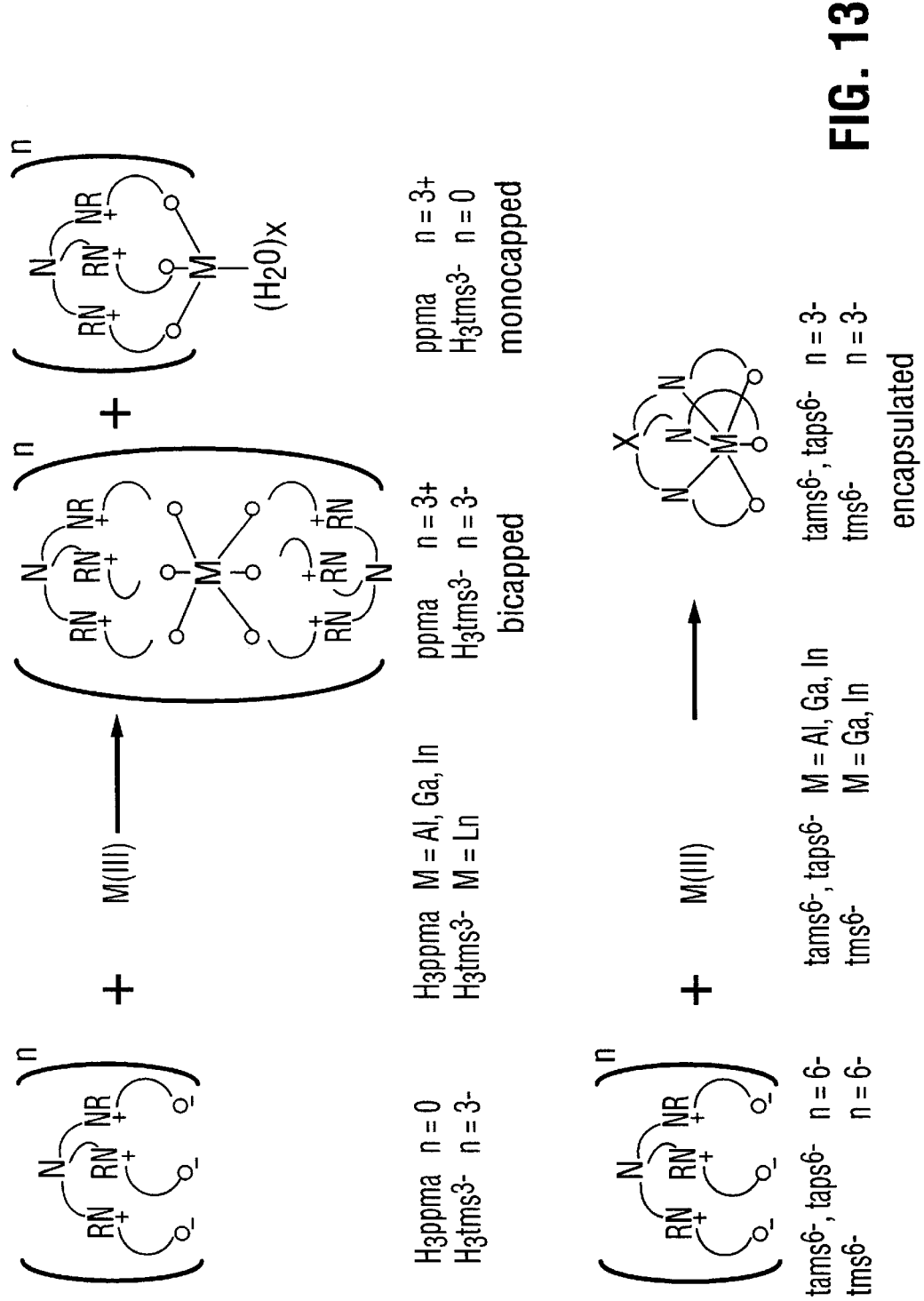
FIG. 13 illustrates a graphical scheme for complexing bicapped, monocapped, and encapsulated configurations.

In an effort to gain some further insight into the aqueous chemistry of $H_6$trns with the lanthanides, the aqueous lanthanide coordination chemistry of two other smaller tripodal aminephenol ligands, $H_6$tams and $H_6$taps (see FIG. 12), has been investigated herein. Should these ligands coordinate in a similar manner as $H_3$trns$^{3-}$ (bicapped), 14 and 13-membered chelate rings would be formed upon lanthanide coordination. The inventors herein were interested in the effect of the large chelate ring size on metal ion stability and selectivity. There has been no structural chemistry reported for either the Ln-tams or Ln-taps systems. However, as was seen with the group 13 metals,[6] variations in the number of potential donor atoms, the number of chelate rings formed upon coordination, and the size of the chelate rings formed (5- or 6-membered rings) can have a profound effect upon metal ion selectivity and coordination geometry (see FIG. 13). Instead this change in backbone results in a dramatic change in binding modality in that $H_6$tams and H6taps react with Ln(III) ions in the presence of base to form encapsulated complexes wherein all 6 donor atoms of the ligand (i.e. $N_3O_3$ coordination) coordinate to the lanthanide ion. This change in coordination mode relative to $H_6$trns (capped, bicapped) also produces a lower selectivity for heavy lanthanide chelation.

Changing the phenolic oxygen donor atoms of $H_6$trns to phosphinic acids, $H_3$ppma (see FIG. 12), resulted in bicapped binding for the group 13 metals (see FIG. 13).[4] The first stepwise equilibrium constant $K_1$ (formation of the monocapped species) is less than that of the second $K_2$ (formation of the bicapped species). This behavior was also noted in the lanthanide $H_3$trns$^{3-}$ system. It was found that the difference between $K_1$ and $K_2$ increased as the metal ion size increased. In light of this size effect, we wished to further explore this phenomenon by using larger metal ions, i.e. the lanthanides. Reported here are the results of the reactions of Ln(III) with $H_3$ppma where, once more, bicapped species are formed. The anomalous equilibrium constant behavior was also observed and is discussed in relation to the similar trend observed for $H_6$trns, whereby the anomaly can be described in terms of hydrophobic effects.

EXAMPLES

Materials. Sodium deuteroxide (NaOD, 40%), deuterium chloride (DCl, 12M) and the lanthanide atomic absorption standards were obtained from Aldrich. Hydrated lanthanide nitrates and chlorides were obtained from Alfa. Deuterium oxide ($D_2O$) and methanol-$d_4$ ($CD_3OD$) and DMSO-$d_6$ were purchased from Cambridge Isotope Laboratories. All were used without further purification. Tris(4-phenylphosphinato-3-methyl-3-azabutyl)amine trihydrochloride monohydrate ($H_3$ppma-3HCl $H_2O$),[8] 1,1,1-tris(((2-hydroxy-5-sulfobenzyl)amino)methyl)ethane dihemihydrate ($H_6$tams.2.5$H_2O$)[6] and 1,2,3-tris((2-hydroxy-5-sulfobenzyl)amino)propane dihemihydrate ($H_6$taps.2.5H2O)[6] were prepared as described in earlier papers.

Instruments. $^1$H NMR spectra (200 and 300 MHz) were referenced to DSS or TMS and recorded on Bruker AC-200E and Varian XL 300 spectrometers. $^{13}$C NMR (75.5 MHz, referenced to DSS or TMS), $^{31}$P NMR (121.0 MHz, referenced to external 85% $H_3PO_4$), natural abundance $^{17}$O NMR (40.7 MHz, referenced to $H_2O$), and 139La NMR (42.4 MHz, referenced to 0.1 M La(ClO$_4$) in 1 M HClO$_4$) spectra were recorded on the latter instrument. Mass spectra were obtained on a Kratos Concept II H32Q (Cs$^+$, LSIMS) instrument with thioglycerol or 3-nitrobenzyl alcohol as the matrix. Infrared spectra were obtained as KBr disks in the range 4000–400 cm$^{-1}$ on a Galaxy Series 5000 FTIR spectrometer. Analyses for C, H, and N were performed.

Synthesis of Lanthanide-$H_3$ppma Complexes. The preparation of the lutetium complex (as the trihydrate) is representative for the lanthanides Er—Lu and the preparation of the terbium complex (as the pentahydrate) is representative for the lanthanides Sm—Ho, Yb, Lu (in the case of Sm, Eu and Ho the metal chloride was used). All the complexes prepared and their elemental analyses, mass spectral, infrared and NMR data are listed in Tables 1–4.

[Lu($H_3$ppma)J[NO$_3$]$_3$.3$H_2O$. The pH of an aqueous solution (4 mL) of $H_3$ppma.3HCl.$H_2O$ (0.200 g, 0.257 mmol) and Lu(NO$_3$)$_3$.6$H_2O$ (0.060 g, 0.128 mmol) was raised to 2.0 using 3M NaOH. Colorless prisms deposited after 2 hours; these prisms were filtered and dried under vacuum to yield 0.145 g (66.0%). Yield for Yb 78.4%, Tm 50.2%, Er 53.0%.

[Tb($H_3$ppma)$_2$[NO$_3$]$_3$.5$H_2O$. An aqueous solution (0.7 mL) of $H_3$ppma.3HCl.$H_2O$ (0.100 g, 0.128 mmol) was added to Tb(NO$_3$)$_3$.5$H_2O$ (0.057 g, 0.128 mmol) in 0.7 mL of $H_2O$. Colorless hexagonal crystals deposited after 24 hours; these were filtered and dried under vacuum to yield 0.064 g (57.6%). Yields for Lu 70.5%, Yb 73.4%, Ho 43.2%, Dy 50.1%, Gd 63.1%, Eu 40.3%, Sm 47.9%.

NMR Measurements. The variable pH 1H NMR spectra of the $H_6$tams and $H_6$taps complexes were run in $D_2O$ with the pD values being measured by a Fisher Accumet 950 pH meter employing an Accumet Ag/AgCl combination microelectrode. The pD values were converted to pH by adding 0.40 to the observed reading.[5] The 17O NMR experiments with Dy(III) were recorded at 21° C., with a spectral window of 1000 Hz, a 90° pulse width of 18 ms, and an acquisition time of 0.256 s; this gave 512 data points. Two thousand transients were collected per spectrum. The 17O linewidths for $H_2O$ were about 60 Hz. Concentrations employed ranged from 1 to 40 mM. The dysprosium induced shifts (DIS) were obtained from the observed shift by making a correction for the bulk magnetic susceptibility of the solution.[6] Stock solutions were prepared from metal nitrates in $D_2O$ ($H_2O$) and the metal-ligand solutions were prepared by pipetting required amounts of stock solution and adjusting the pH with acid or base. In the equilibrium measurements, the ionic strength was controlled by addition of NaCl.

For the Ln-$H_3$ppma (Ln=Yb, Lu) equilibrium constant studies using 31P{H} NMR, conditions as described in a previous publication were used.[8] Metal ion stock solutions (50 mM) were prepared from the hydrates of $Lu(NO_3)_3$ and $Yb(NO_3)_3$. All solutions contained a fixed amount of $M^{3+}$ (25 mM) with the ligand concentration varied ($R=[L]_T/[M]_T$) as $0.25<R<4$. Solutions were made up to a volume of 0.8 mL and the pH was adjusted to 1.5. The solutions were allowed to equilibrate for 48 hours prior to the spectra being collected. The respective peak integrals enabled a quantitative measurement (long delay times of 1.6 s were employed) of free ligand ([L]). The knowledge of [L] allowed $\bar{n}$, the ratio of bound ligand to total metal to be calculated ($\bar{n}=([L]_T-[L])/[M]_T$). A plot of $\bar{n}$ vs. [L] resulted in a curve from which the variables $\beta_1$ and $\beta_2$ could be calculated using computer curve fitting software.

Potentiometric Equilibrium Measurements. The procedure was the same as detailed in a previous paper.[7] The measurements were made at $25.0\pm0.1°$, m=0.16 M NaCl. The $pK_a$s of the ligands were checked whenever a different synthetic batch of ligand was used, and fresh ligand solutions were always employed (For $H_6$taps: $pK_a1=1.7$, $pK_a2=6.54$, $pK_a3=7.78$, $pK_a4=8.73$, $pK_a5=9.77$, $pK_a6=11.24$ and for $H_6$tams: $pK_a1=2.92$, $pK_a2=6.56$, $pK_a3=7.95$, $pK_a4=8.91$, $pK_a5=9.81$, $pK_a6=1.19$).[6] The lanthanide solutions were prepared by dilution of the appropriate atomic absorption standards. Since the lanthanides do not hydrolyze below pH 6, the excess acid in the solutions could be obtained by titrating with standard NaOH and analyzing for the strong acid by the method of Gran.[7]

The ratio of ligand to metal used was 1:2<L:M<4:1. Concentrations were in the range 0.5–2.5 mM. A minimum of five titrations were performed for each metal. The metal - $H_6$taps and metal - $H_6$tams solutions were titrated to just beyond six equivalents $NaOH/(H_{6taps\ (H}tams)$, because of slow hydrolysis beyond this point. Although complexation was rapid (1–3 min per point to give a stable pH reading), care was taken to ensure that no trace hydrolysis or precipitation was occurring by monitoring up to 30 minutes for pH drift. The protonation constants for the lanthanide-ligand stability constants were determined by using the program BEST.8 $H_6$tams and $H_6$taps, both reacted with Ln(III) to coordinate as hexadentate ligands, liberating six equivalents of acid per ligand. Typically 100 data points were collected with about 80–90% of the points being in the buffer region of metal-ligand complexation and the remaining points in the strong acid region being used as a check of excess acid concentration.

X-ray Crystallographic Analyses of $[C_{60}H_{90}LuN_8O_{12}]$ $(NO_3)_3.3H_2O$. Selected crystallographic data appear in Table 5. The final unit-cell parameters were obtained by least-squares on the setting angles for 25 reflections with 2=55.7–68.7°. The intensities of three standard reflections, measured every 200 reflections throughout the data collection, decayed linearly by 2.7%. The data were processed[9] and corrected for Lorentz and polarization effects, decay, and absorption (empirical, based on azimuthal scans).

The structure of $[C_{60}H_{90}LuN_8O_{12}](NO_3)_3.3H_2O$ was solved by the Patterson method. The structure analysis was initiated in the centrosymmetric space group R c on the basis of the E-statistics, this choice being confirmed by subsequent calculations. The nitrate anions and water molecules were modeled as (1:1) disordered about a point of $S_6$ symmetry. Because of thermal motion and near overlap of disordered components, the nitrate groups deviate from ideal geometry. Refinement of the structure in the noncentrosymmetric space group R3c failed to resolve the disorder. All non-hydrogen atoms were refined with anisotropic thermal parameters. Hydrogen atoms were fixed in calculated positions (N—H=0.91 Å, C—H=0.98 Å, $B_H=1.2\ B_{bonded\ atom}$).

A correction for secondary extinction (Zacharaisen type) was applied, the final value of the extinction coefficient being $1.73(3)\times10^{-7}$. Neutral atom scattering factors for all atoms[10] and anomalous dispersion corrections for the non-hydrogen atoms[11] were taken from the *International Tables for X-Ray Crystallography*. Selected bond lengths and bond angles appear in Table 6. Complete tables of crystallographic data, final atomic coordinates and equivalent isotropic thermal parameters, anisotropic thermal parameters, bond lengths, bond angles, torsion angles, intermolecular contacts, and least-squares planes are included as Supporting Information.

Results $[Ln(H_3ppma)_2]^{3+}$ (Ln=Lu—Sm). The synthesis of the bisligand complexes as hydrated salts was achieved by mixing stoichiometric (L:M=2:1) amounts of aqueous solutions of metal nitrate or chloride and $H_3$ppma (with Er—Lu the pH was raised to 1.5). Precipitation of the resulting complexes occured within a few hours to days, depending on the metal ion. The lanthanide complexes fall into two categories: the complexes of the smaller, heavier lanthanides (Er—Lu) were prepared in the same manner as their group 13 metal analogs[8] yielding cubic crystals, which analyzed as trihydrates. The complexes of the lighter lanthanides (Sm—Ho, and Yb, Lu for comparison) were prepared in a similar manner, however, no pH adjustment was made. Hexagonal plates were obtained; these analyzed as pentahydrates (and when a starting material metal chloride was used, two additional hydrochlorides were found). It is expected that this additional hydration is due to a different crystal lattice formed at lower pH, however the thin plates proved unsuitable for X-ray analysis. The IR spectra of the Er—Lu complexes resembled their group 13 analogs, with one of the three P—O stretches shifted to lower wavenumber as the metal ion increased in size, a trend which persisted through the lanthanide series from samarium to lutetium ($V_{PO=}$ 1154–1165 $cm^{-1}$). The P—O stretch at the highest wavenumber for the trihydrates, when Ln=Er-Lu ($V_{PO}=$ 1194–1190 $cm^{-1}$) changed for the pentahydrates of the earlier lanthanides Ln=Sm—Ho and Yb, Lu ($V_{PO}=$ 1183–1180 $cm^{-1}$) likely due to a slight change in structure ($.3H_2O$ vs. $.5H_2O$). It is unclear whether this is attributable to differences in hydrogen bonding or to a different coordination number; however, a large shift in the $V_{NH}$ stretch ($\Delta V_{NH}$ 300 $cm^-$) along with a change of $V_{PO}$ indicated a change in hydrogen bonding strength. The LSIMS (+) mass spectra showed molecular ions $[ML_2-2H]^+$ and $[ML_2-H]^{2+}$ at the appropriate m/z value for the bicapped species, and ions for the monoligand species $[ML-2H]^+$ and for the free ligand $[L+H]^+$ at m/z=651.

Figure 2:
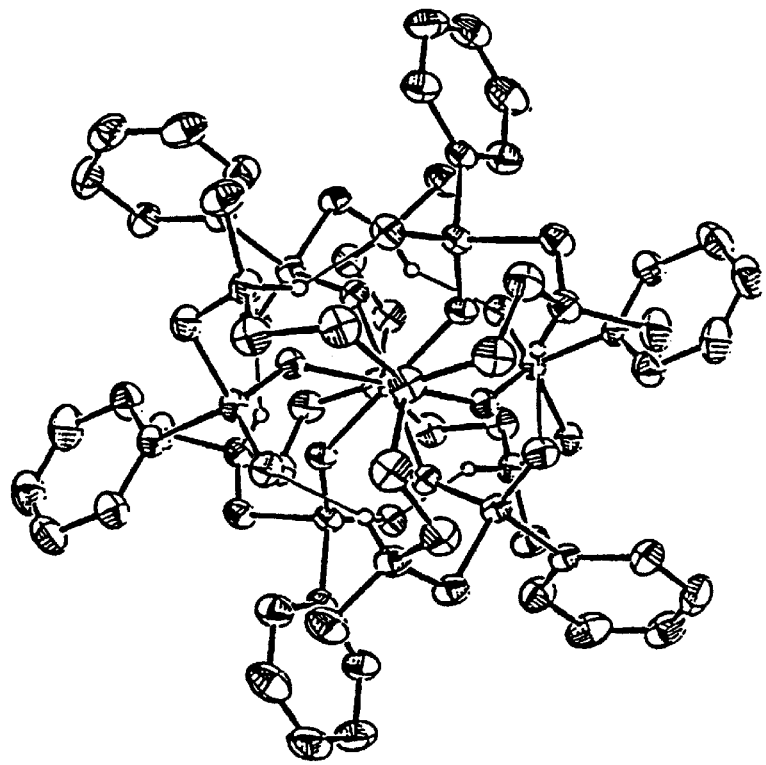
FIG. 2 depicts an ORTEP representation of the cation in [Lu(H$_3$ppma)$_2$](NO$_3$)$_3$.3H$_2$O (25 % probability thermal ellipsoids). View approximately down the threefold axis.

X-ray Crystal Structure of $[Lu(H_3ppma)_2][NO_3]_3.3H_2O$. Colorless prisms crystallized in the space group R c. ORTEP representations of the $[Lu(H_3ppma)_2]^{3+}$ cation is shown in FIGS. 1 and 2, and selected bond distances and angles are listed in Table 6. The structure is of a bicapped $ML_2$, similar to that observed for the bisligand tren-based aminephenolate-lanthanide complexes[5e] and is isostructural and isomorphous with the indium structure previously reported.[8] The complex cation has exact $S_6$ symmetry. The O—Lu—O trans angle is crystallographically imposed at 180.0°, and the cis O—Lu—O angles are 88.72(6) and 91.28(6)°, resulting in near perfect octahedral geometry, expected because the ionic radius[12] of $Lu^{3+}$ (0.861 AÅ) is similar to that of $In^{3+}$ (0.800 Å) i.e. the ideal size to accommodate two ligands in a bicapped manner. The Lu—O distances of 2.190(2) Å are in the expected range, although few six-coordinate lutetium structures have been reported. This distance is only slightly longer than the In—O distance (2.117(3) Å) in the indium structure,[8] again reflecting the similar size of the ions. On coordination to the metal ion, the phosphorus atoms are rendered chiral, with one half of the bicapped structure possessing all R chirality and one half all S, i.e. the cation is the RRRSSS diastereomer. This opposing RRRSSS chirality generates the six fold symmetry and is indeed necessary to accommodate the six bulky phenyl rings because, once the phosphinates coordinate, the phenyls completely engulf the coordination sphere. Highly ordered intramolecular hydrogen bonding is observed from the protonated nitrogen N(2) to the phosphinate oxygen O(2) on an adjacent arm, where H . . . O=1.87 Å (N . . . O=2.684(3) Å) and N—H . . . O=147°.

Figure 3A:
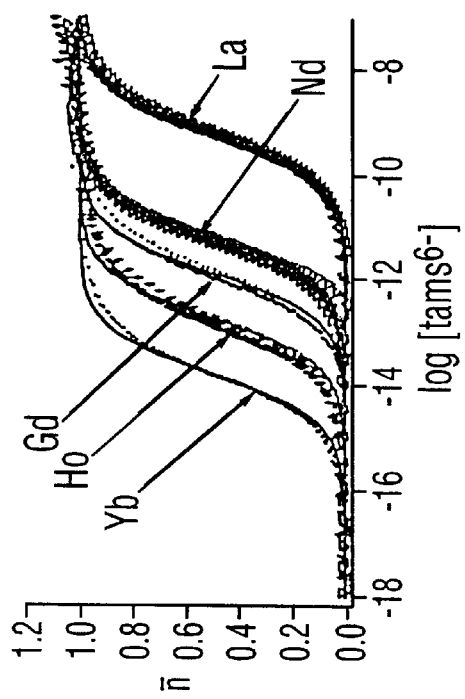
FIGS. 3(a) and 3(b) represent experimental lanthanide titration curves at 2 mM H$_6$tams: 2 mM Ln(III) (top) and 2 mM H$_6$taps: 2 mM Ln(III) (bottom).a=moles of NaOH/ moles of ligand.
Figure 3B:
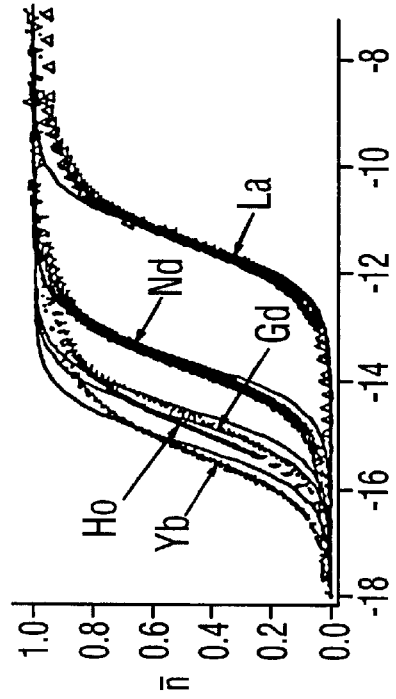

Formation Constants FIG. 3 shows experimental titration curves for the lanthanides with $H_6$tams (top) and $H_6$taps (bottom) at a ratio of 2 mM Ln(III):2 mM ligand. The following equilibrium conventions apply to these two systems, i.e.

(1)

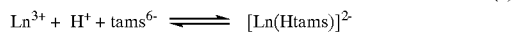

(2)

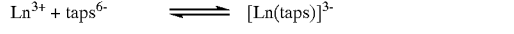

(3)

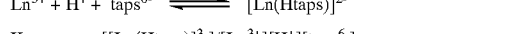

(4)

Figure 4A:
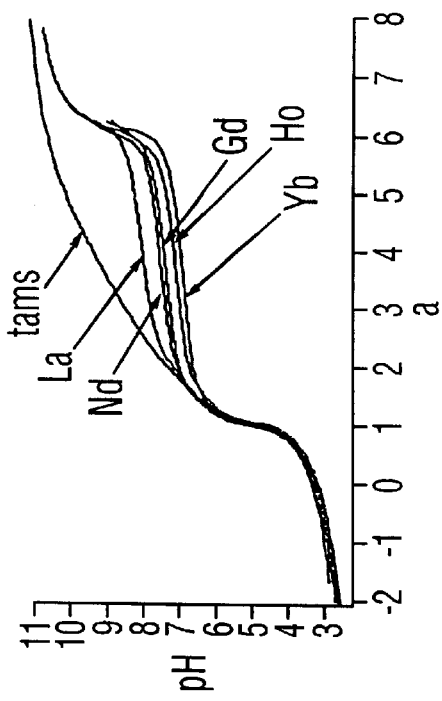
FIGS. 4(a) and 4(b) represent experimental plots of n (the ratio of bound ligand to total metal ion concentration) vs. log [tams$^{6-}$] (top) and ñ vs. log [taps$^{6-}$] (bottom); the solid lines were generated using the calculated stability constants, $K_{Ln(tams)}$ and $K_{Ln(taps)}$.
Figure 4B:
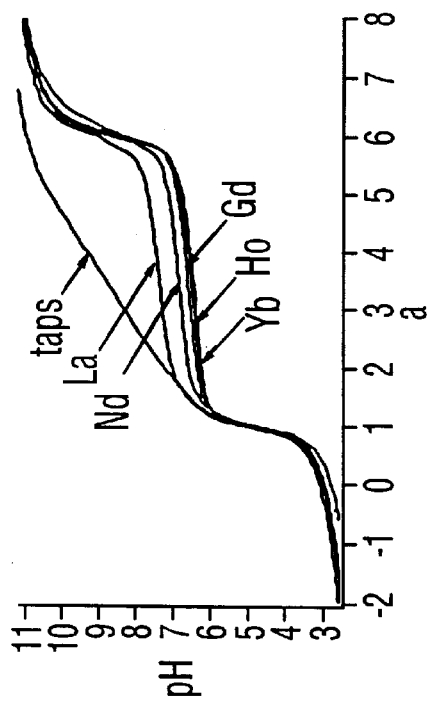

The curves show plateaus which extend up to a=6 indicating that the ligands are coordinating in a hexadentate fashion through all six $N_3O_3$ donor atoms; this is verified (and further emphasized) in the ñ plots (FIG. 4) where the curves rise to ñ=1 and then plateau, even in the experiments with excess ligand. Analysis of the potentiometric data gave the stability constants listed in Table 7. It was necessary to include monoprotonated complexes in the model to improve the fit of the data, although these only form to a small extent (maximum~25% of total Ln(III)). Both tams$^{6-}$ and taps$^{6-}$ are selective for the heavier lanthanides, but much less so than is $H_3$trns$^{3-}$.[7]

Figure 5:
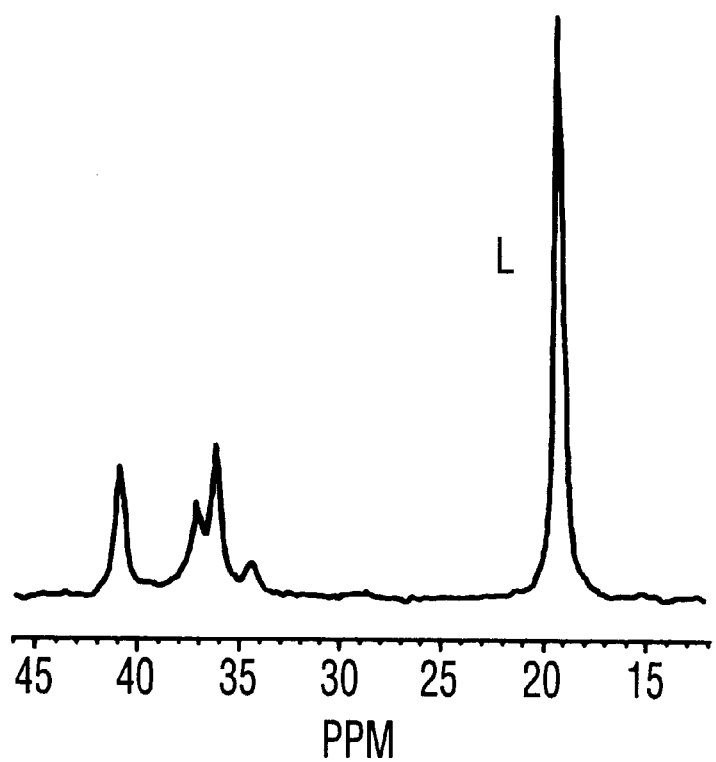
FIG. 5 illustrates $^{31}$P (121.0 MHz) NMR spectrum for the stability constant study of the Yb(III)/H$_3$ppma system, R=[L]$_T$/[M]$_T$=3.8.

Because of the very low p$K_a$'s for $H_3$ppma,[8] formation constants for the ytterbium and lutetium complexes of $H_3$ppma were determined by a $^{31}$P NMR approach highlighted previously.[8] $^{31}$P NMR spectra were recorded for a series of solutions (R=[L]$_T$/[M]$_T$, L=$H_3$ppma, M=Yb, Lu) in the range 0.24<R<3.80 (where [Lu]=[Yb]=25 mM). A representative sample for the Yb study is shown in FIG. 5. The resonance for free $H_3$ppma is clearly distinct from those of the metal complexes (ML and ML$_2$). Two resonances for both RRRSSS and RRSSSR diastereomers were noted, as was seen in the group 13 study. It is much more difficult to assign these resonances as specific 1:1 and 2:1 species (c.f. the case of the group 13 metals where the additional tool of the metal NMR was invaluable), however the concentration of free ligand [L] is readily obtained from the integrals. From this value, ñ can be calculated for each experiment (see experimental and ref. 8). Assuming the formation of the 1:1 and 2:1 complex (equations 5 and 6) where M=Yb, Lu and L=$H_3$ppma, and using mass balance equations, ñ (the ratio of bound ligand to total metal) can be expressed as equation 7 in terms of the formation constants $\beta_1$, $\beta_2$ and free ligand [L].

(5)

(6)

$$\tilde{n} = (\beta_1[L] + 2\beta_2[L]^2)/(1 + \beta_1[L] + \beta_2[L]^2)$$

(7)

Figure 6:
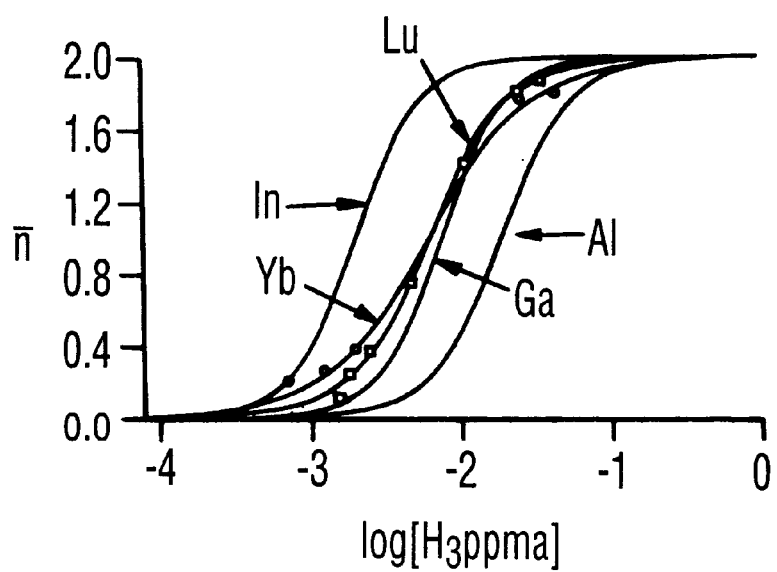
FIG. 6 illustrates a plot of ñ vs. [H$_3$ppma] for the Yb(III) (○) and Lu(III) (□) systems (solid lines indicate fits, symbols indicate experimental data). The calculated curves for the group 13 metal ions[8] are included for comparison.

From a plot ñ vs. [L] values of the formation constants are obtained for Lu are log $\beta_1$=1.79 (7), log $\beta_2$=4.40 (2) and for Yb log $\beta_1$=2.25 (7), log $\beta_2$=4.42 (5). A plot of ñ vs. log [L] for Lu and Yb (also included is the data[8] for Al, Ga and In) is shown in FIG. 6. The curves rise to ñ=2 and then plateau, indicating formation of a 2:1 species.

Multinuclear NMR ($^1$H, $^{13}$C, $^{31}$P, $^{139}$La). Solution NMR studies on the Ln(III)-$H_6$tams and Ln (III)-H6taps systems were unrevealing. The $^1$H NMR and $^{13}$C NMR spectra of [Lu(taps)]$^{3-}$ in D$_2$O at pD 9 showed a series of broad overlapping resonances characteristic of fluxional behavior. The $^1$H NMR spectra of [Lu(tams)]$^{3-}$, [La(tams)]$^{3-}$, and [La(taps)]$^{3-}$ were similar to those of the free ligand suggesting fast exchange. A $^{139}$La NMR study of 30 mM La(III):30 mM $H_6$taps as a function of pH showed only one resonance at 0 ppm, the chemical shift of La$_{(aq)}^{3+}$. The linewidth of this resonance increased with pH suggesting that [La(taps)]3- is in exchange with La$_{(aq)}^{3+}$.

Figure 7:
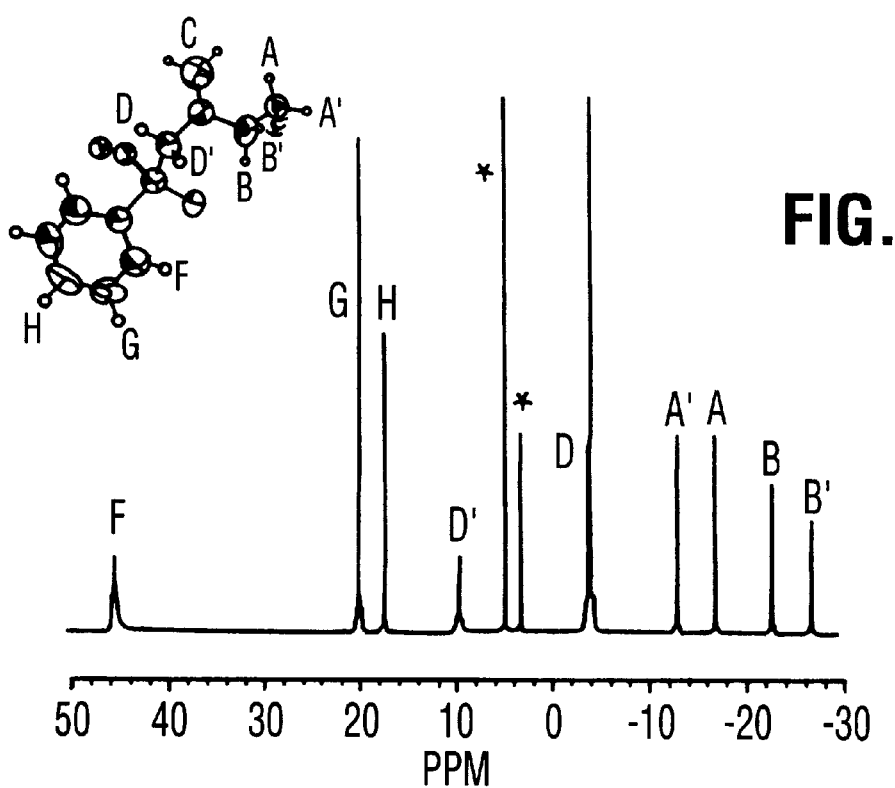
FIG. 7 illustrates $^1$H NMR spectrum (300.0 MHz) of [Tm(H$_3$ppma)$_2$](NO$_3$)$_3$ in CD$_3$OD (δ corrected for Δ$_χ$ the shift due to the bulk magnetic susceptibility). *=solvent.

The $^1$H NMR spectra of the [Ln(H$_3$ppma)$_2$]$^{3+}$ complexes in CD$_3$OD where Ln=Er—Lu, all exhibit ten resonances, corresponding to the ten hydrogens labeled in FIG. 7, the spectrum of the thulium complex. The observance of only 10 resonances clearly indicates the persistence of the S$_6$ symmetry in solution for all these H$_3$ppma complexes. The spectrum of the diamagnetic lutetium complex greatly resembles those obtained for the same structure with the group 13 metals,[8] and is most similar to that of the indium complex, consistent with the similar ionic radii of the two metals. The resonances can be readily assigned from their coupling patterns (Lu), from their 2D $^1$H—$^1$H COSY spectra, and from comparison with the group 13 metal complexes of H$_3$ppma. With the paramagnetic lanthanide (Er—Yb) complexes, dramatic chemical shifts are noted, with well resolved and narrow resonances. The $^{31}$P NMR spectra of these four late lanthanide complexes also exhibit the S$_6$ symmetry in solution, showing a single narrow resonance for all six equivalent phosphorus atoms.

On moving to the larger lighter lanthanides (Sm—Ho) a dramatic change in the respective $^1$H/$^{31}$P NMR spectra is noted. The $^{31}$P NMR spectra no longer indicate a single species in solution, (four resonances are usually observed) resulting in a proliferation of resonances in the corresponding $^1$H NMR spectra. The chemical shifts of the 31P NMR resonances suggest that only complexes are present, i.e. no resonance for free H$_3$ppma is evident, and thus one must assume that the solvent CD$_3$OD is interacting with the bicapped complex forcing changes in geometry and/or stoichiometry. Even from these complex spectra, the 10 resonances corresponding to the RRRSSS diastereomer can usually be picked out when the lanthanide in question causes sufficient chemical shift separation (Tb—Ho). If a different solvent is used, i.e. DMSO-d$_6$, a dramatic simplification of the spectrum is observed. Ten resonances (broader than in CD$_3$OD) of the RRRSSS diastereomer are observed in the $^1$H NMR spectrum, along with the spectrum of H$_3$ppma. This is reciprocated in the $^{31}$P NMR spectrum where two resonances are seen, one of which is present in the CD$_3$OD spectrum and a new one of free H$_3$ppma. Interestingly, if the Yb and Lu complexes are prepared in the same manner as Sm—Ho, i.e. no pH adjustment, as hexagonal crystals (analyzing as the pentahydrate), their respective NMR spectra are the same as those obtained by raising the pH (as the trihydrate) i.e. no decomposition or rearrangement is noted, which suggests the lanthanide is sufficiently small and/or tightly bound to prevent solvent interaction with metal ion.

The shift, Δ, induced at a nucleus of a ligand binding to a Ln(III) cation can be expressed as the sum of the diamagnetic shift ($\Delta_d$), the contact shift ($\Delta_c$), the pseudocontact shift ($\Delta_p$), and the shift due to the bulk magnetic susceptibility ($\Delta_c$), equation (8).

$$\Delta = \Delta_d + \Delta_c + \Delta_p + \Delta \quad (8)$$

$$\Delta_c = 4\pi C(\mu_{eff}/2.84)^2/3T \quad (9)$$

The diamagnetic shift, which is usually relatively small, can be obtained from the shift of [Lu(H$_3$ppma)$_2$]$^{3+}$. Since the magnetic moments of the Ln(III) ions are relatively constant, the bulk magnetic susceptibility shift can be estimated from equation (9)[13] which applies to a superconducting solenoid, where C is the concentration (mM) of Ln(III), m$_{eff}$ is the effective magnetic moment for Ln(III), and T is the temperature (K). Calculated m$_{eff}$ values were taken from Figgis.[14] The contact and pseudocontact shifts can be expressed by equation (10)[17] where D$_c$ and D$_p$ are each expressed as the product of two terms.

$$\Delta' = \Delta - (\Delta_d + \Delta) = \Delta_c + \Delta_p = <S_z>F + C^D G \quad (10)$$

The first term ($<S_z>$ or $C^D$) is characteristic of the lanthanide, but independent of the ligand, while the second term (F or G) is characteristic of the ligand in question, but independent of the Ln(III) cation. Values for the lanthanide dependent contact term, $<S_z>$, and pseudocontact term, $C^D$, have been calculated.[19-23],[15,16,17,18,19] Equation (10) can be separated into two linear forms, equations (11) and (12). Although, both (11) and (12) are mathematically identical, Reilley et al[20] have advocated the use of equation (11) when F>>G (and equation (12) when G>>F) since the dependence on theoretical $C^D$ (or $<S_z>$) will be minimized by a small intercept.

$$\Delta'/C^D = F(<S_z>/C^D) + G \quad (11)$$

$$\Delta'/<S_z> = G(C^D/<S_z>) + F \quad (12)$$

Figure 8A:
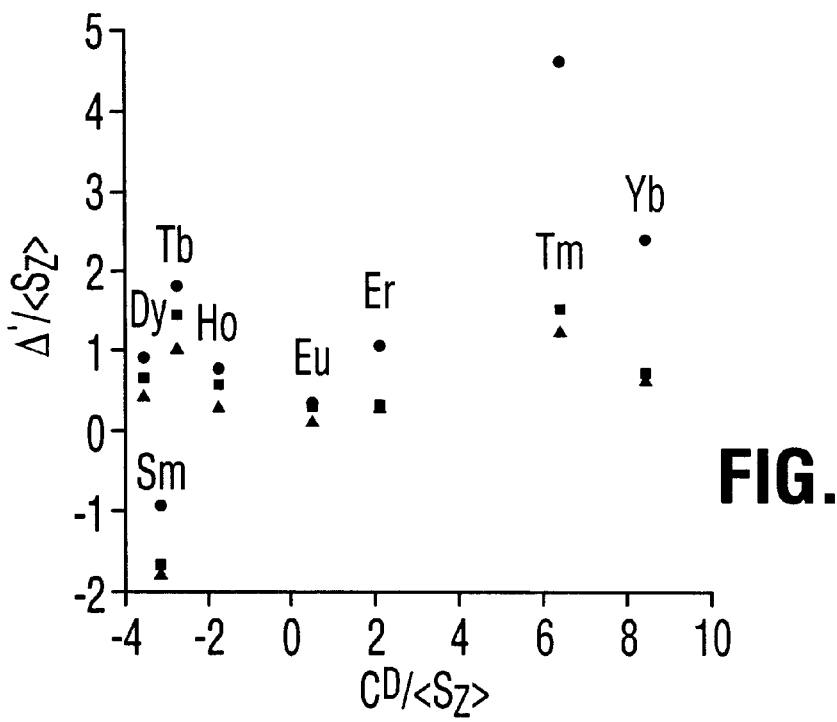
FIGS. 8(a) and 8(b) depict a plot of Δ/C$^D$ vs. <S$_z$>/C$^D$ for the $^1$H NMR spectra (top: ●=hydrogen H$_F$, ■=H$_G$, and ▲=H$_H$) and for the $^{31}$P NMR spectra (bottom) of [Ln (H$_3$ppma)$_2$]$^{3+}$ where Ln=Sm—Lu.
Figure 8B:
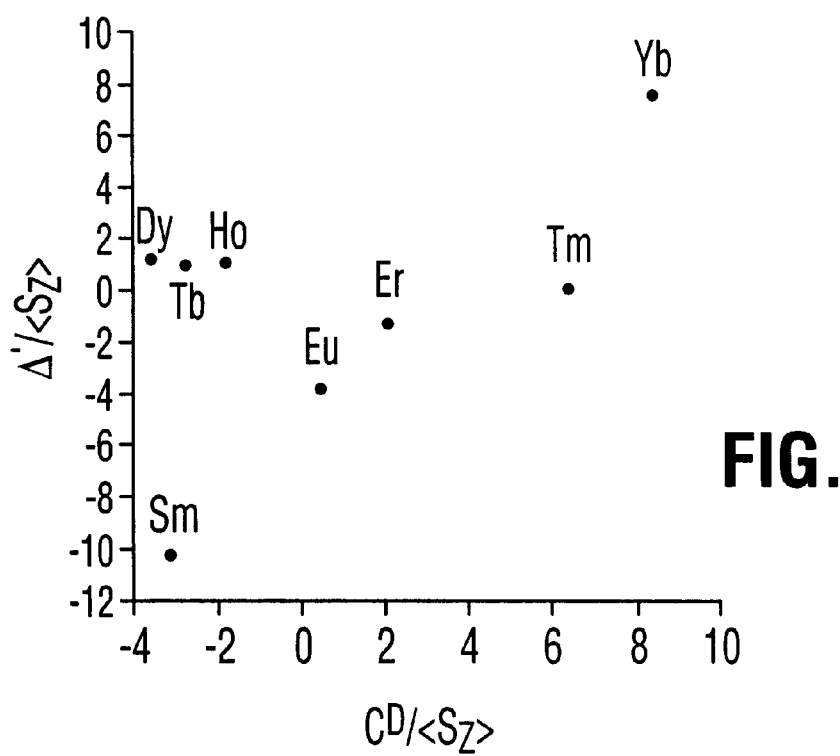

FIG. 8 shows a plot of D'/$C^D$ vs. $<S_z>$/$C^D$ for the $^1$H NMR spectra (top) and for the 31P NMR spectra (bottom). For an isostructural series a linear relationship is expected, whereby the parameters F and G may be obtained from slopes and intercepts of plots derived from equation 11 or 12. This is clearly not observed in the structures presented herein. A difference from Er—Yb vs. Sm—Ho would be expected as analysis reveals additional water in the solid state, however a correlation for Er—Yb would be certainly assumed as all evidence points to an "isostructural miniseries", it is evident from these plots that there must be some change in ligand orientation.

Figure 9:
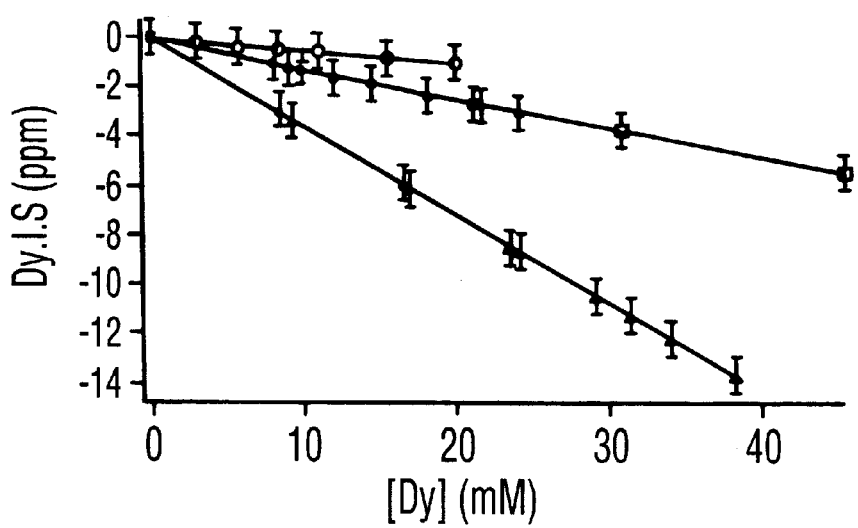
FIG. 9 depicts a plot of Dy.I.S. vs. [Dy(III)] (mM) for Dy$_{(aq)}^{3+}$, ●, [Dy(TAMS)]$^{3-}$, ●, [Dy(TAPS)]$^{3+}$, □, and [Dy(H$_3$TRNS)$_2$]$^{3-}$, ○. Error bars represent linewidths at half height.

$^{17}$O NMR: The natural abundance 17O NMR of water in the presence of a lanthanide ion and ligand gives a qualitative picture of complexation. Peters and coworkers have exploited the dysprosium induced shift of water (Dy.I.S.) to estimate quantitatively the number of bound water molecules associated with various lanthanide complexes.[25-27],[21,22],[23] The Dy.I.S. of water was measured at varying dysprosium concentrations. The plot of Dy.I.S. versus [Dy(III)] was linear with a slope of −358 ppm/M. It had been previously established that the contact contribution in a paramagnetic Ln(III)-induced shift of a Ln(III)-bound 17O nucleus is almost independent of the nature of the probed O-containing ligand in question and of other co-ligands coordinated to the lanthanide.[26],[24] Since the $^{17}$O shift is predominantly contact in nature, the slope of a plot of Dy.I.S versus [Dy(III)] should be proportional to the number of bound water molecules associated with the complex. If the hydration number of Dy(III) is taken to be eight,[25] then a slope of −358/8=−45 would be indicative of one bound water and each multiple of 45 corresponds to one water. FIG. 9 shows the Dy.I.S. versus [Dy(III)] for Dy$_{(aq)}^{3+}$, [Dy(tams)]$^{3-}$ and [Dy(taps)]$^{3-}$ ([Dy(H$_3$trns)$_2$]$^{3+}$ is shown for comparison). The slope of −358 ppm/M for Dy$_{(aq)}^{3+}$ is in excellent agreement with that obtained by Alpoim et al[25] (−357 ppm/M) and by Reuben and Fiat[26] (−360 ppm/M). The error bars show the linewidths at half height (60 Hz); however, the precision was ±5 Hz. All three plots were linear with correlation coefficients of greater than 0.999. The slopes for [Dy(tams)]$^{3-}$ and [Dy(taps)]$^{3-}$ were −128 ppm/M (2.8 H$_2$O) and −123 ppm/M (2.7 H$_2$O), respectively. Ratios of tams$^{6-}$:Dy(III) and taps$^{6-}$:Dy(III) as high as 8 showed a limiting stoichiometry of 1 tams$^{6-}$:1 Dy(III) and 1 taps$^{6-}$:1 Dy(III). A study of the hydration of the Dy—H$_3$ppma system was attempted; however, even at large excesses of ligand, multiple species were present.

Discussion

We have discovered that H$_3$ppma forms highly (S$_6$) symmetrical bis(ligand) complexes with the lanthanides Sm—Lu, analogous to those formed with the group 13 metals.[8] Indeed, the X-ray structure of the lutetium complex is isostructural and isomorphous with that of the indium structure. The high symmetry is preserved in solution, indicated in the $^1$H and $^{31}$P NMR spectra. Such evidence indicates an isostructural series of compounds from and Sm—Lu. In light of this, it was expected that the paramagnetic shifts of the $^1$H and $^{31}$P resonances could be resolved into contact and pseudocontact components, once corrected for diamagnetic and bulk magnetic susceptibility contributions. However, a linear relationship for $\Delta'/C^D$ vs. $<S_z>$/$C^D$ (or $\Delta'/<S_z>$ vs. $C^D/<S_z>$) was not forthcoming. Such a failure to correlate is usually a result of changing coordination geometry or number. In the case of H$_3$ppma all evidence (NMR, mass spectral, IR and elemental analyses) points towards an isostructural series, especially for Er—Lu. It is evident that subtle changes in ligand orientation about the paramagnetic lanthanide as the ionic radius increases causes sufficiently large changes in chemical shift, to prevent a linear correlation, i.e. the interlocking phenyl groups must move further apart to some extent to accommodate the larger metal ion, even if the change in ionic radius is only small. The opposite of this, i.e. the compression of the phenyl rings was the rational for the greater stability of the indium complex with respect to the gallium and aluminum.[8] Indeed the chemical shift of the hydrogens ortho to phosphorus in the phenyl rings (H$_F$) show a progressive shift to lower frequency Al—Ga—In—Lu. For these small changes in geometry to cause such a large effect suggests a large pseudocontact contribution to the chemical shift, as it is this contribution which contains structural information. It is stated[17,24,25] that if geometric information for a substrate is to be obtained, the complex must have axial symmetry (at least three fold), it would be expected that the $S_6$ symmetry here would be more than sufficient.

The bis(ligand) complexes obtained for $H_3$ppma are similar to those obtained[7] with $H_3$trns$^{3-}$. In this latter case the oxygen donor group is phenolato as opposed to phosphinato. Similar anomalous behavior was observed in the formation constants of the mono vs. bisligand complexes, i.e. $K_2$ was found to be greater than $K_1$, an unusual occurrence, demanding explanation. In the $H_3$trns$^{3-}$:Ln(III) system,[7] it was thought likely that this unusual phenomenon was predominantly an entropic effect; the nature of the $H_3$trs$^{3-}$:Ln(III) system suggests that there should be no favorable enthalpy associated with $K_2$ (relative to $K_1$) based on electrostatic arguments, and a lowering of coordination number. As the first equivalent of $H_3$trns$^{3-}$ displaced 3 waters, while the second equivalent displaced 5 waters, this second equilibrium increased the translational entropy of the system more than the first, and was thus manifested in the larger value of $K_2$. This argument was supported by calorimetric measurements, which showed $\Delta S_2 > \Delta S_1$ for each Ln(III) studied.

An alternative argument can be proposed for the anomalous $K_2 > K_1$ effect based upon the hydrophobic effect.[27,28] Consider the solvation of a gaseous hydrocarbon in water at 25° C. This process involves a small negative enthalpy of solvation, but a larger negative entropy of solvation; it is thermodynamically disfavored because of entropy.[32] The aggregation of apolar solutes is then driven by entropy such that the water molecules avoid entropically unfavorable interactions with the apolar solute molecules. $H_3$trns$^{3-}$ and $H_3$ppma can be thought of as ampiphilic species with charged polar regions and three apolar aryl rings. Describing the two equilibria, $K_1$ and $K_2$, pictorially as in FIG. 10 for $H_3$ppma (the charges differ for $H_3$trns$^{3-}$) leads to a hydrophobic interpretation of the two complexation reactions. The areas shaded in grey represent the hydrophobic aryl portions of the molecules.

In the first step ($K_1$) one ion with a hydrophobic region combines with a lanthanide ion to give a molecule with a hydrophobic region. The second step ($K_2$) is the combination of a monoligand species with a second ligand, each with a hydrophobic region, combining to give an ion with only one hydrophobic region. This minimization of solvent ($H_2O$) accessible hydrophobic regions, or "a tightening of the hydrophobic belt", should be reflected in a more positive entropy for $K_2$ relative to $K_1$, as was observed for $H_3$trns$^{3-}$. Both steps are also enthalpically favored by the formation of Ln—O (phenolate) bonds. This hydrophobic interpretation of the complexation can also be invoked to explain the similar anomalous behavior on the equilibria of the ligand $H_3$ppma when complexed to the group 13 metals.[8] Topologically the ligand is almost identical to that of trns$^{6-}$, having a tripodal tren-based structure bearing pendant donors incorporating a hydrophobic aryl region. $H_3$ppma reacts with the group 13 metals and with the lanthanides to form capped and bicapped complexes by coordinating to the metal through the phosphinato oxygen atoms. The second stepwise equilibrium constant is markedly greater than the first in the case of the group 13 metals and less so, but still significantly large, in the case of the lanthanides.

Figure 10:
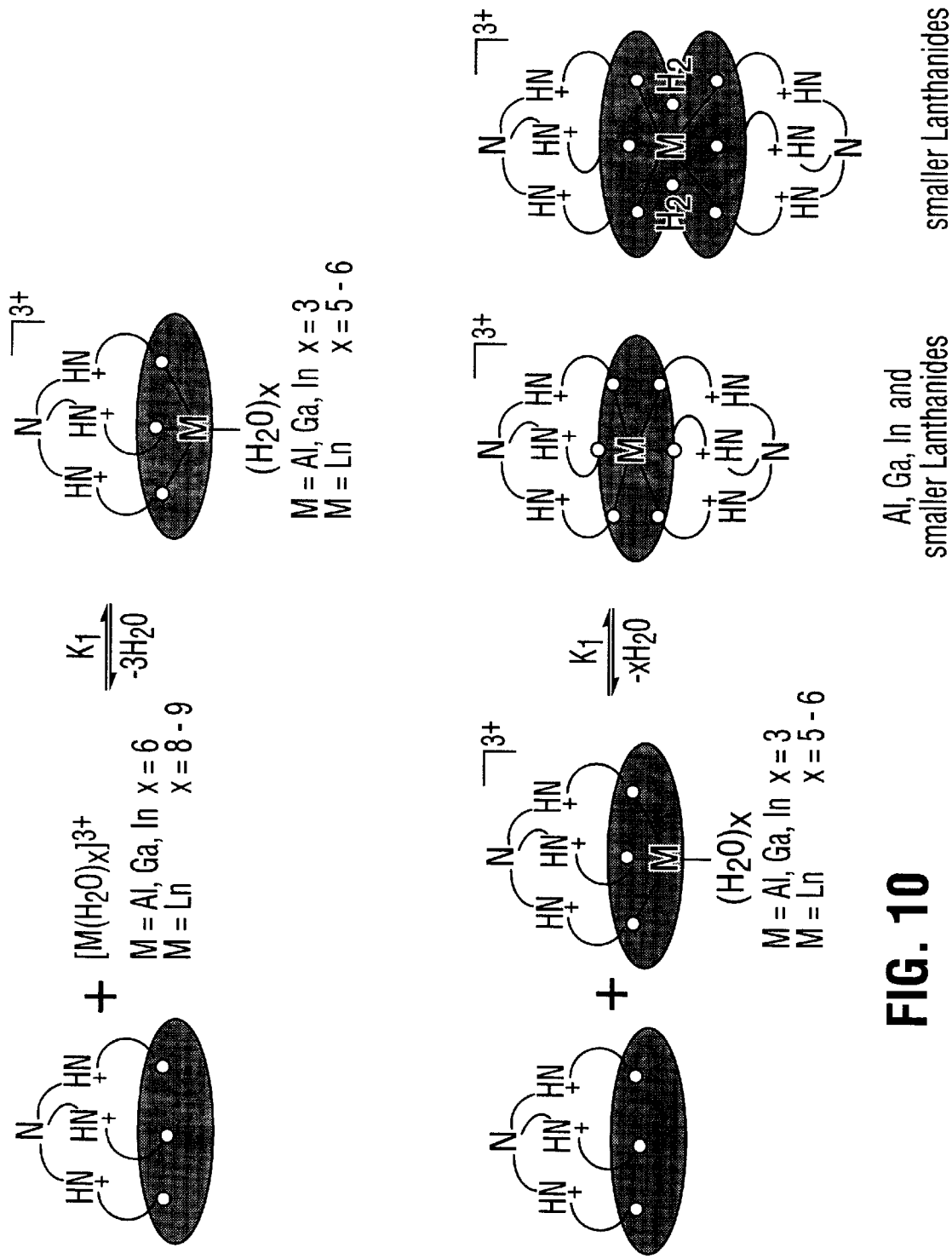
FIG. 10 illustrates tightening the hydrophobic belt: the Ln(III)—H$_3$ppma (or H$_3$trns$^{3-}$) equilibria viewed in terms of hydrophobic interactions.

Since the aquo ions of Al(III), Ga(III), and In(III) are known to be six coordinate and the bicapped complexes contain octahedral ions, the argument presented previously for trns$^{6-}$ i.e. for an inner sphere desolvation and lowering of coordination number does not apply. However this anomalous behavior can be rationalized by the hydrophobic effect as shown in FIG. 10. In the case of the lanthanides, a reduction of solvation may play a part, but again it is likely that this hydrophobic explanation is applicable. The difference in $K_2$ vs. $K_1$ is not as startling as for the group 13 metals even though the formation of a six-coordinate lanthanide complex would be expected to exhibit an even greater entropic effect on moving from a monocapped species with the expulsion of 5 bound waters. The major difference is this case is the increase in size of the coordinated metal ion. $H_3$ppma showed an increased affinity for the larger metals in group 13, where $\log_2$ for In>Ga>Al, with an increase by an order of magnitude in each case. The preference for indium was attributed to the ionic radii of the metals, indium being of ideal size to accommodate the bulky phenyl groups on coordination. The determination of the formation constants of the group 13 metals was carried out via a combined 31P—$^{27}$Al/$^{17}$Ga NMR spectroscopic method, as the use of more conventional methods (potentiometry) was obviated by the very low $pK_a$'s of the phosphinic hydroxyls and lack of chromophores (UV/Vis). In the case of the lanthanide complexes, the study was restricted to diamagnetic Lu(III) and paramagnetic Yb(III). Attempts with any earlier lanthanides were thwarted by increasing line widths and overlapping of resonances. Even so, a trend is noted, which can be readily explained by considering the "tightening of hydrophobic belt". Indium, it would appear, is the ideal size to accommodate the six phenyl rings in a strain-free manner, whilst still excluding solvent from the coordination sphere. The lanthanides show an marked increase in $K_1$ with respect to the group 13 metals, which can be attributed to their increased ionic radii. The larger the metal ion, the further apart the two ligands become, thus allowing more solvent to be in contact with the hydrophobic areas of the complex (FIG. 10), hence the hydrophobic belt is somewhat loosened. This is reflected in the decrease in $K_1$ relative to $K_2$ as we move from Yb(III) to Lu(III), indeed it appears that on moving to the larger lanthanides (Ho—Sm) the phenyls will be sufficiently separated to perhaps allow water coordination, or at least interference of solvent causing a break up of the complexes, as was highlighted by the $^1$H and $^{31}$P NMR spectra of these complexes in $CD_3OD$. This may also be the cause of the non-correlation of the lanthanide induced shift NMR data.

When $H_3$trs$^{3-}$ binds to a lanthanide(III) in a tridentate fashion, there should be no chelate effect–three sixteen membered chelate rings are formed. Given the relatively high stability found for these capped 16-membered ring complexes,[7] there must be an effect which predisposes the ligand to a binding posture. The flexibility imparted by a loose H-bond network coupled with the large chelate ring size results in a tridentate ligand which should have little or no strain energy created in accommodating different Ln(III) ions; thus the increase in stability is purely electrostatic and increases with the inverse ionic radius of the lanthanide considered. In order to further explore the effect of large chelate ring size on Ln(III) selectivity, solution studies with $H_6$tams and H6taps were undertaken. If these two ligands reacted in the same manner as $H_6$trns, then lanthanide complexes containing 14-membered and 13-membered chelate rings would be formed. Instead of coordinating solely through the phenolato donor atoms, tams$^{6-}$ and taps$^{6-}$ coordinated through the three amino nitrogen and three phenolato oxygen donor atoms. A major difference between $H_6$trns and $H_6$tams or $H_6$taps is the microscopic order of deprotonation. It had been shown that the first three deprotonation events of $H_6$trns occur at phenolic sites,[7] whereas $H_6$tams and $H_6$taps are firstly deprotonated at an ammonium site, followed by three phenol sites, and then the remaining two ammonium groups.[6] The first deprotonation of $H_6$tams and $H_6$taps occurs at a pH much lower than that at which Ln(III) complexation occurs. Hence coordination to this amino group should be facile. Coordination to one amino group would necessarily bring the remaining ammonium groups closer to the metal ion to allow for proton displacement and lanthanide coordination to give the observed $N_3O_3$ ligand donor set. Variation of the donor group in changing from $H_3$trns3− to $H_3$ppma, i.e. from phenolato to phosphinato showed no dramatic change in coordination as shown for tams6− and taps$^{6-}$. Indeed, none is expected as both ligands have nitrogen $pK_a$'s which are higher than the oxygen $pK_a$'s, the much lower phenolato and phosphinato $pK_a$'s dictate binding to the lanthanides exclusively through oxygen.

Figure 11:
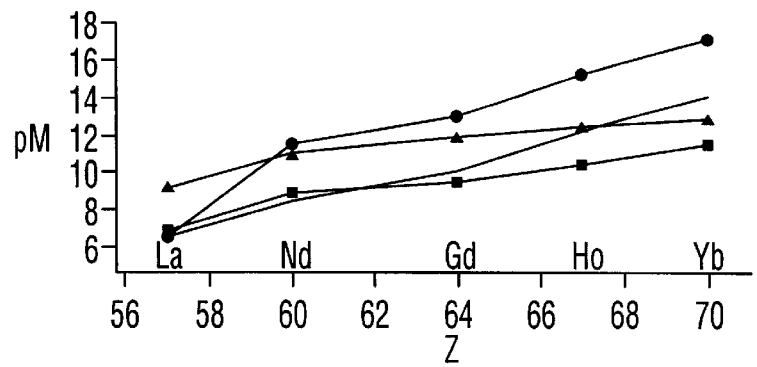
FIG. 11 depicts comparative pM values vs. Z for H$_3$trns$^{3-}$ ([Ln(III)]$_{tot}$=1 mM), ●, ([Ln(III)]$_{tot}$=1 μM), ⊖, taps6- ([Ln(III)]$_{tot}$=1 mM), ▲, tams6- ([Ln(III))]$_{tot}$=1 mM),■.

The 17O NMR study of both [Dy(tams)]$^{3-}$ and [Dy(taps)]$^{3-}$ indicated the presence of three inner sphere water molecules, implying a 9-coordinate Dy(III) in each of the complexes. The change in coordination mode from $H_3$trns$^{3-}$ to tams$^{6-}$ and taps$^{6-}$ has a profound effect on the metal ion selectivity. There is a large increase in stability upon going from La(III) to Nd(III) for all three ligands. However, on going from Nd(III) to Yb(III), $H_3$trns$^{3-}$ exhibited a selectivity of about 2 log units per lanthanide studied. Here tams$^{6-}$ exhibits lesser selectivity, about one log unit per lanthanide studied, whereas taps$^{6-}$ has a much lower selectivity between Gd(III) and Yb(III). A better way of analyzing the data is to take into account the competition with hydrogen ion for the ligand by calculating pM values where pM=−log $[M_{free}]$. This gives an impression of the relative sequestering ability of the ligands under a standard set of conditions. In FIG. 11, pM values are calculated at pH 7.4 for a ligand to metal ratio of 10:1. The total concentration of Ln(III) is set at 1 mM; however since the stability constants for $H_3$trns$^{3-}$ have an inverse square dependence on [$H_3$trns$^{3-}$], the pM values for [Ln]$_{tot}$=1 mM have also been calculated to highlight this dilution effect. At millimolar concentrations and above, $H_3$trns$^{3-}$ is the best ligand for complexing Nd(III)ⓇYb(III), and its sequestering ability increases with atomic number, Z. The much flatter curve for taps6− indicates that it is less able to discriminate between the lanthanides.

The major structural difference between taps$^{6-}$ and tams$^{6-}$ is that taps$^{6-}$ coordinates to a lanthanide forming four 6- and two 5-membered chelate rings, whereas tams$^{6-}$ forms only 6-membered chelate rings upon coordination. An established tenet of coordination chemistry is that 5-membered chelate rings are more stable than 6-membered chelate rings and this difference in stability increases with increasing metal ion size.[33] This effect is manifested here where [Ln(taps)]$^{3-}$ complexes are 1–2 orders of magnitude more stable than the analogous [Ln(tams)]$^{3-}$ complexes.

TABLE 1

Elemental Analyses for [Ln($H_3$ppma)$_2$](X)$_3$.Y$H_2$O (X = NO$_3$, Cl)

| Formula | C Calc | C Found | H Calc | H Found | N Calc | N Found |
|---|---|---|---|---|---|---|
| $C_{60}H_{90}LuN_{11}O_{21}P_6$.3$H_2$O | 41.99 | 41.88 | 5.64 | 5.87 | 8.98 | 8.95 |
| $C_{60}H_{90}LuN_{11}O_{21}P_6$.5$H_2$O | 41.13 | 41.26 | 5.75 | 5.65 | 8.79 | 8.55 |
| $C_{60}H_{90}N_{11}O_{21}P_6$Yb.3$H_2$O | 42.04 | 42.34 | 5.64 | 5.60 | 8.99 | 8.91 |
| $C_{60}H_{90}N_{11}O_{21}P_6$Yb.5$H_2$O | 41.17 | 41.19 | 5.76 | 5.62 | 8.80 | 8.68 |
| $C_{60}H_{90}N_{11}O_{21}P_6$Tm.3$H_2$O | 42.14 | 42.24 | 5.66 | 5.61 | 9.01 | 8.79 |
| $C_{60}ErH_{90}N_{11}O_{21}P_6$.3$H_2$O | 42.18 | 41.88 | 5.66 | 5.87 | 9.02 | 8.95 |
| $C_{60}Cl_3H_{90}HoN_8O_{12}P_6$.5$H_2$O.2HCl | 41.52 | 42.06 | 5.92 | 6.15 | 6.46 | 6.24 |
| $C_{60}DyH_{90}N_{11}O_{21}P_6$.5$H_2$O | 41.42 | 41.66 | 5.79 | 6.04 | 8.86 | 8.50 |
| $C_{60}H_{90}N_{11}O_{21}P_6$Tb.5$H_2$O | 41.51 | 41.23 | 5.81 | 5.85 | 8.87 | 8.59 |
| $C_{60}GdH_{90}N_{11}O_{21}P_6$.5$H_2$O | 41.55 | 41.61 | 5.81 | 5.63 | 8.88 | 8.53 |
| $C_{60}Cl_3EuH_{90}N_8O_{12}P_6$.5$H_2$O.2HCl | 41.84 | 41.99 | 5.97 | 6.10 | 6.50 | 6.25 |
| $C_{60}Cl_3H_{90}N_8O_{12}P_6$Sm.5$H_2$O.2HCl | 41.87 | 42.13 | 5.97 | 6.14 | 6.51 | 6.38 |

TABLE 2

+LSIMS Mass Spectral Data for [LnL$_2$]$^{3+}$ (L = $H_3$ppma) Complexes

| | [ML$_2$-2H]$^+$ | [ML-2H]$^+$ | [ML$_2$-2H]$^{2+}$ |
|---|---|---|---|
| Lu* | 1473 | 823 | 778 |
| Yb* | 1472 | 822 | 737 |
| Tm | 1467 | 817 | 734 |
| Er | 1466 | 816 | 733 |
| Ho | 1463 | 813 | 733 |
| Dy | 1462 | 812 | 731 |
| Tb | 1457 | 807 | 729 |
| Gd | 1456 | 806 | 728 |
| Eu | 1451 | 801 | 726 |
| Sm | 1450 | 800 | 726 |

*Identical spectrum obtained for trihydrate and pentahydrate

TABLE 3

IR data (cm$^{-1}$) for [Ln($H_3$ppma)$_2$](X)$_3$.Y$H_2$O (X = NO$_3$ or Cl†; Y = 3 or 5‡) in cm$^-$

| | $v_{OH/NH}$ | $\delta_{NH}$ | $v_{NO_3}$ | $v_{PO}$ | $v_{PC/PPh}$ |
|---|---|---|---|---|---|
| Lu | 3435,2614 | 1642 | 1386 | 1194,1136,1065 | 745,720,579,560 |
| Lu‡ | 3431,2426 | 1643 | 1385 | 1182,1137,1062 | 740,719,580,553 |
| Yb | 3455,2621 | 1644 | 1385 | 1193,1135,1062 | 743,718,579,559 |
| Yb‡ | 3429,2441 | 1643 | 1384 | 1181,1136,1062 | 741,720,580,553 |
| Tm | 3429,2615 | 1644 | 1386 | 1194,1135,1063 | 745,718,580,559 |
| Er | 2454,2614 | 1641 | 1386 | 1192,1134,1061 | 743,718,578,559 |
| Ho†‡ | 3442,2413 | 1644 | | 1183,1134,1060 | 740,719,580,553 |
| Dy‡ | 3431,2426 | 1644 | 1364 | 1181,1134,1058 | 741,718,580,555 |
| Tb‡ | 3429,2410 | 1643 | 1386 | 1180,1034,1058 | 740,718,580,553 |
| Gd‡ | 3423,2445 | 1644 | 1384 | 1180,1035,1057 | 740,718,580,553 |
| Eu†‡ | 3443,2445 | 1643 | | 1180,1035,1055 | 740,718,580,553 |
| Sm†‡ | 3418,2460 | 1650 | | 1180,1133,1054 | 741,717,580,559 |

TABLE 4

$^1$H and $^{31}$P NMR Chemical Shifts[a] for
[Ln(H$_3$ppma)$_2$](NO$_3$).3H$_2$O in CD$_3$OD (Ln = Er – Lu)
NMR spectra were referenced to TMS in CD$_3$OD (insert) and
chemical shifts were corrected for bulk magnetic susceptibility $\Delta_x$

|   | [Tm(H$_3$ppma)$_2$]$^{3+}$ | [Er(H$_3$ppma)$_2$]$^{3+}$ | [Yb(H$_3$ppma)$_2$]$^{3+}$ | [Lu(H$_3$ppma)$_2$]$^{3+}$ |
|---|---|---|---|---|
| H$_A$  | −17.04 | −5.97 | −0.27 | 3.24 |
| H$_{A'}$ | −13.06 | −3.93 | 0.44 | 2.37 |
| H$_B$  | −22.92 | −7.91 | −0.63 | 4.74 |
| H$_{B'}$ | −26.94 | −8.69 | −0.76 | 3.00 |
| H$_C$  | −4.24 | −0.02 | 1.88 | 3.03 |
| H$_D$  | −3.80 | −1.93 | 2.14 | 2.30 |
| H$_{D'}$ | 9.39 | 5.00 | 3.19 | 3.00 |
| H$_F$  | 45.08 | 23.25 | 13.59 | 7.50 |
| H$_G$  | 19.69 | 12.23 | 9.22 | 7.46 |
| H$_H$  | 17.07 | 11.2 | 8.83 | 7.34 |
| P    | 14.61 | −6.86 | 34.41 | 15.29 |

[a]For labelling see FIG. 7.

TABLE 5

Selected Crystallographic Data for Lu[(H$_3$ppma)$_2$](NO$_3$)$_3$ 3H$_2$O

| Compound | [C$_{60}$H$_{90}$LuN$_8$O$_{12}$](NO$_3$)$_3$.3H$_2$O |
|---|---|
| Formula | C$_{60}$H$_{96}$LuN$_{11}$O$_{23}$P$_6$ |
| fw | 1716.29 |
| Crystal system | Trigonal |
| Space group | R$\overline{3}$ c |
| a, Å | 19.060(1) |
| c, Å | 36.395(3) |
| V, Å$^3$ | 11449(1) |
| Z | 6 |
| ρcalc, g/cm$^3$ | 1.493 |
| T, °C. | 21 |
| Radiation | Cu |
| λ, Å | 1.54178 |
| μ, cm$^{-1}$ | 43.66 |
| Transmission factors | 0.82–1.00 |
| R (F) | 0.024 |
| R$_w$ (F) | 0.025 |

R = Σ||F$_o$| − |F$_c$||/Σ|F$_o$|, R$_w$ = (Σw(|F$_o$| − |F$_c$|)$^2$/Σw|F$_o$|$^2$)$^{1/2}$.

TABLE 6

Selected Bond Lengths (Å) and Angles (deg)*
for [Lu(H$_3$ppma)$_2$](NO$_3$)$_3$.3H$_2$O

Lengths

| Atom | Atom | Distance | Atom | Atom | Distance |
|---|---|---|---|---|---|
| Lu(1) | O(1) | 2.190(2) | P(1) | O(1) | 1.492(2) |
| P(1)  | O(2) | 1.487(2) | P(1) | C(4) | 1.826(3) |
| P(1)  | C(5) | 1.786(3) | N(1) | C(1) | 1.471(3) |
| N(2)  | C(2) | 1.518(3) | N(2) | C(3) | 1.498(4) |
| N(2)  | C(4) | 1.506(3) |      |      |          |

Angles

| Atom | Atom | Atom | Angle | Atom | Atom | Atom | Angle |
|---|---|---|---|---|---|---|---|
| O(1) | Lu(1) | O(1)[a] | 88.72(6) | O(1) | Lu(1) | O(1)[b] | 180.0 |
| O(1) | Lu(1) | O(1)[c] | 91.28(6) | O(1) | P(1)  | O(2)  | 119.1(1) |
| O(1) | P(1)  | C(4)    | 103.5(1) | O(1) | P(1)  | C(5)  | 108.41(10) |
| O(2) | P(1)  | C(4)    | 109.8(1) | O(2) | P(1)  | C(5)  | 111.3(1) |
| C(4) | P(1)  | C(5)    | 103.5(1) | Lu(1)| O(1)  | P(1)  | 145.2(1) |
| C(1) | N(1)  | C(1)[a] | 108.7(2) | C(2) | N(2)  | C(3)  | 111.5(2) |
| C(2) | N(2)  | C(4)    | 110.2(2) | C(3) | N(2)  | C(4)  | 110.7(2) |

TABLE 6-continued

Selected Bond Lengths (Å) and Angles (deg)*
for [Lu(H$_3$ppma)$_2$](NO$_3$)$_3$.3H$_2$O

| N(1) | C(1) | C(2) | 113.4(2) | N(2) | C(2) | C(1) | 113.1(2) |
|---|---|---|---|---|---|---|---|
| P(1) | C(4) | N(2) | 112.6(2) | P(1) | C(5) | C(6) | 121.8(2) |
| P(1) | C(5) | C(10) | 119.5(2) | | | | |

*[a] −y, x − y, z
[b] −x, −y, 1 · z
[c] y, −x + y, 1 − z.

TABLE 7

Log Formation Constants for Ln(III) with tams$^{6-}$ and taps$^{6-}$ at 25° C.,
$\mu$ = 0.16 M NaCl

| | TAMS$^{6-}$ | | TAPS$^{6-}$ | |
|---|---|---|---|---|
| Ln(III) | ML/M · L | HML/ML · H | ML/M · L | HML/ML · H |
| La | 9.17 (1) | — | 11.33 (3) | 7.14 (2) |
| Nd | 11.19 (6) | — | 13.59 (3) | 6.54 (3) |
| Gd | 11.86 (9) | 6.55 (9) | 14.50 (1) | 6.38 (4) |
| Ho | 12.71 (10) | 6.69 (4) | 14.71 (4) | 6.44 (9) |
| Yb | 13.78 (1) | 6.33 (3) | 15.15 (3) | 6.39 (4) |

Conclusion

The complexation properties of an N$_4$O$_3$ tripodal aminomethylene phosphinato ligand, tris(4-phenylphosphinato-3-methyl-3-azabutyl)amine (H$_3$ppma), with the lanthanides have been investigated. H$_3$ppma forms mono- and bis (ligand) complexes when Ln=Sm–Lu. The formation constants of the Lu (log $_1$=1.79, log $_2$=4.40) and the Yb (log $_1$=2.25, log $_2$=4.42) complexes were determined in aqueous solution at pH=1.5 using a 31P NMR spectroscopic method. The bis(ligand) complex is highlighted by the molecular structure of the lutetium complex [Lu(H$_3$ppma)$_2$](NO$_3$)$_3$.3H$_2$O (C$_{60}$H$_{96}$LuN$_{11}$O$_{24}$P$_6$), which has been solved by X-ray methods; the complex crystallizes in the trigonal space group R c, a=19.060(1) Å, c=36.395(3) Å, Z=6. The structure was solved by Patterson methods and was refined by full-matrix least-squares procedures to R=0.024 (R$_w$= 0.040) for 2061 reflections with I>3 (I). The structure of the biscomplex showed the ligand to coordinate in a tridentate manner through the three phosphinate oxygens, resulting in a bicapped octahedral structure of exact S$_6$ symmetry, which is preserved in solution as shown by $^1$H and $^{31}$P NMR spectroscopies (CD$_3$OD, DMSO-d$_6$).

The ligand H$_3$ppma has been shown to form S$_6$ symmetric bicapped bis(ligand) complexes with the lanthanides, (as seen in the X-ray crystal structure of the lutetium complex, and in solution NMR studies) whereby it binds as a tridentate ligand exclusively via the phosphinato groups. These complexes are isostructural with those obtained with the group 13 metals[8] and similar to those obtained when the oxygen donor is phenolato.[7]

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

References 1. (a) Perl, D. P. *Environ. Health Perspect.* 1985, 63, 149. (b) Crapper-McLachlan, D. R. *Neurobiol. Aging* 1986, 7, 525. (c) Liss, L. *Aluminum Neurotoxicity*; Pathotox Publishers: Park Forest, Ill., 1980.
2. (a) Welch, M. J.; Moerlein, S. M. *In Inorganic Chemistry in Biology and Medicine*; Martell, A. E., Ed.; American Chemical Society: Washington, D.C., 1980; p. 121. (b) Green, M. A.; Welch, M. J. *Nucl. Med. Biol.* 1989, 16, 435. (c) Zhang, Z.; Lyster, D. M.; Webb, G. A.; Orvig, C. *Nucl. Med. Biol.* 1992, 19, 327.
3. (a) Martin, R. B.; Richardson, F. S. *Q. Rev. Biophys.* 1979, 12, 181. (b) Meares, C. F.; Wensel, T. G. *Acc. Chem. Res.* 1984, 17, 202. (c) *Lanthanide Probes in Life, Chemical, and Earth Sciences*; Bunzli, J.-C. G.; Choppin, G. R., Eds.; Elsevier: Amsterdam, 1989. (d) Bunzli, J.-C. G. *Inorg. Chim. Acta* 1987, 139, 219. (e) Horrocks, W. D. J.; Albin, M. *Prog. Inorg. Chem.* 1984, 31, 1. (f) Gupta, R. K.; Gupta, P. J. *J. Mag. Reson.* 1982, 47, 344. (g) Pike, M. M.; Springer, C. S. *J. Mag. Reson.* 1982, 46, 348. (h) Sherry, A. D.; Geraldes, C. F. G. C.; Cacheris, W. P. *Inorg. Chim. Acta* 1987, 139, 137.
4. Lauffer, R. B. *Chem. Rev.* 1987, 87, 901.
5. (a) Liu, S.; Wong, E.; Karunaratne, V.; Rettig, S. J.; Orvig, C. *Inorg. Chem.* 1993, 32, 1756. (b) Liu, S.; Wong, E.; Rettig, S. J.; Orvig, C. *Inorg. Chem.* 1993, 32, 4268. (c) Liu, S.; Rettig, S. J.; Orvig, C. *Inorg. Chem.* 1992, 31, 5400. (d) Liu, S.; Gelmini, L.; Rettig, S. J.; Thompson, R.C.; Orvig, C. *J. Amer. Chem. Soc.* 1992, 114, 6081. (e) Liu, S.; Yang, L.-W.; Rettig, S. J.; Orvig, C. *Inorg. Chem.* 1993, 32, 2773. (f) Berg, D. J.; Rettig, S. J.; Orvig, C. *J. Amer. Chem. Soc.* 1991, 113, 2528. (g) Smith, A.; Rettig, S. J.; Orvig, C. *Inorg. Chem.* 1998, 27, 3929.
6. Caravan, P.; Orvig, C. *Inorg. Chem.* 1997, 36, 236–248.
7. Caravan, P.; Hedlund, T.; Liu, S.; Sjoberg, S.; Orvig, C. *J. Am. Chem. Soc.* 1995, 117, 11230.
8. Lowe, M. P.; Rettig, S. J.; Orvig, C. *J. Am. Chem. Soc.* 1996, 118, 10446.
9. Glasoe, P. K.; Long, F. A. *J. Phys. Chem.* 1960, 64, 188.
10. Bertini, I.; Luchinat, C. *NMR of Paramagnetic Molecules in Biological Systems*; Benjamin/Cummings: Menlo Park, 1986; Vol. 3.
11. Gran, G. *Acta Chem. Scand.* 1950, 4, 559.
12. Motekaitis, R. J.; Martell, A. E. *Can. J. Chem.* 1982, 60, 2403.
13. *teXsan*: Crystal Structure Analysis Package (1985 & 1992). Molecular Structure Corporation, The Woodlands, Tex.
14. *International Tables for X-Ray Crystallography*, Vol. IV. Kynoch Press, Birmingham, England, 1974. pp. 99–102.
15. *International Tables for Crystallography*, Vol. C. Kluwer Academic Publishers, Boston, 1992. pp. 200–206.
16. Shannon, R. D. *Acta. Crystallogr.* 1976, A32, 751.
17. Peters, J. A.; Huskens, J.; Raber, D. J. *Prog. NMR Spectrosc.* 1996, 28, 283.
18. Figgis, B. N. *Introduction to Ligand Fields*; Robert E. Krieger Publishing Co.: Malabar, Fla., 1986.
19. Golding, R. M.; Halton, M. P. *Aust. J. Chem.* 1972, 25, 2577.
20. Pinkerton, A. A.; Rossier, M.; Spiliadis, S. *J. Magn. Reson.* 1985, 64, 420.
21. Bleaney, B. *J. Magn. Reson.* 1972, 8, 91.
2. Bleaney, B.; Dobson, C. M.; Levine, B. A.; Martin, R. B.; Williams, R. J. P.; Xavier, A. V. *J. Chem. Soc., Chem. Commun.* 1972, 791.
3. Golding, R. M.; Pyykko, P. *Mol. Phys.* 1973, 26, 1389.
4. Reilley, C. N.; Good, B. W.; Allendoerfer, R. D. *anal. Chem.* 1976, 48, 1446.
25. Alpoim, M. C.; Urbano, A. M.; Geraldes, C. F. G. C.; Peters, J. A. *J. Chem. Soc. Dalton Trans.* 1992, 463.
26. Huskens, J.; Kennedy, A. D.; van Bekkum, H.; Peters. J. *J. Amer. Chem. Soc.* 1995, 117, 375.
27. Huskens, J.; Peters, J. A.; van Bekkum, H.; Choppin, G. R. *Inorg. Chem.* 1995, 34, 1756.
28. Peters, J. A.; Kieboom, A. P. G. *Recl. Trav. Chim. Pays-Bas* 1983, 102, 381.
29. Helm, L.; Foglia, F.; Kowall, T.; Merbach, A. E. *J. Phys.: Condens. Matter* 1994, 6, A137.
30. Reuben, J.; Fiat, D. *J. Chem. Phys.* 1969, 51, 4909.
31. Tanford, C. *The Hydrophobic Effect: Formation of Micelles and Biological Membranes*; John Wiley & Sons: New York, 1973.
32. Blokzijl, W.; Engberts, J. B. F. N. *Angew. Chem. Int. Ed. Engl.* 1993, 32, 1545.
33. Hancock, R. D.; Martell, A. E. *Chem. Rev.* 1989, 89, 1875.

What is claimed is:

1. An amine phosphinate tripodal ligand of the formula:

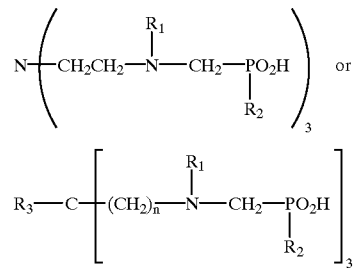

wherein n is 1 or 2, R$_1$ and R$_3$ are H, CH$_3$, C$_2$H$_5$ or other alkyl; and R$_2$ is C$_6$H$_5$, CH$_3$, CH$_2$OH, other alkyl, substituted alkyl, or aryl, and physiologically compatible salts and derivatives thereof.

2. A compound as claimed in claim 1 wherein the amine phosphinate tripodal ligand is:

H3ppma

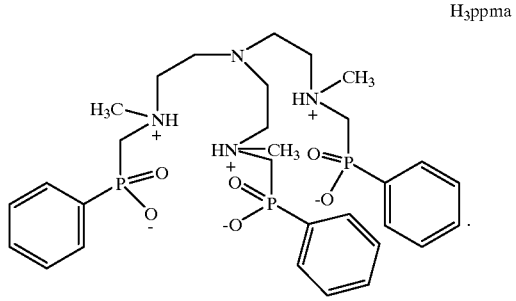

3. A process of preparing an amine phosphinate tripodal ligand of the formula:

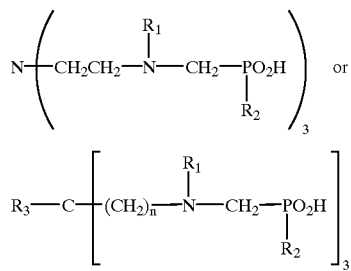

wherein n is 1 or 2, $R_1$ and $R_3$ are H, $CH_3$, $C_2H_5$ or other alkyl; and $R_2$ is $C_6H_5$, $CH_3$, $CH_2OH$, other alkyl, substituted alkyl, or aryl, and physiologically compatible salts and derivatives thereof, which comprises
(a) reacting a tripodal amine of the formula:

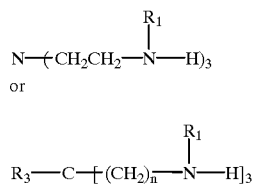

wherein n is 1 or 2, $R_1$ and $R_3$ are H, $CH_3$, $C_2H_5$, or other alkyl; with $H_2P(R_2)O_2$ and $CH_2O$ or $(CH_2O)_m$, wherein $R_2$ is H, $C_6H_5$, $CH_3$, other alkyl, substituted alkyl, or aryl, and m is 2 or greater; or
(b) converting the $R_2$ group of one amine phosphinate tripodal ligand to another $R_2$ group by using formaldehyde or paraformaldehyde.

4. A process of preparing an amine phosphinate tripodal ligand of the formula:

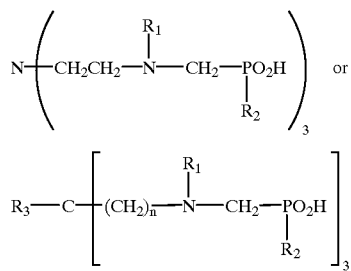

wherein n is 1 or 2, $R_1$ and $R_3$ are H, $CH_3$, $C_2H_5$ or other alkyl; and $R_2$ is $CH_2OH$, and physiologically compatible salts and derivatives thereof, which comprises converting an amine phosphinate tripodal ligand wherein $R_2$ is H to an amine phosphinate tripodal ligand wherein $R_2$ is $CH_2OH$ by reacting with formaldehyde or paraformaldehyde.

5. A process of preparing tris(4-phenyl-phosphinato-3-methyl-3-azabutyl)amine which comprises reacting tris(3-azabutyl)amine with phenylphosphinic acid and formaldehyde.

6. A process of chelating a metal ion which comprises complexing the metal ion with an amine phosphinate tripodal ligand of the formula:

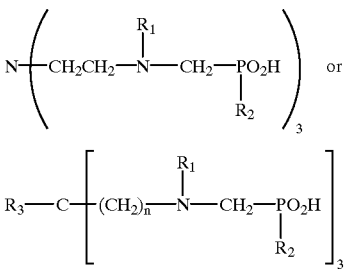

wherein n is 1 or 2, $R_1$ and $R_3$ are H, $CH_3$, $C_2H_5$ or other alkyl; and $R_2$ is $C_6H_5$, $CH_3$, $CH_2OH$, other alkyl, substituted alkyl, or aryl.

7. A process as claimed in claim 6 wherein the metal ion is selected from the group consisting of Tc, Re, the group 13 metals and rare earths.

8. A process of chelating a trivalent metal ion of the group 13 metals and the rare earths which comprises complexing any one of the group 13 metals, Al, Ga and In, and any one of the rare earths, Sc, Y, La, Ce, Pr, Nd, Pm, Sm, Eu, Gd, Tb, Dy, Ho, Er, Tm, Yb and Lu, with an amine phosphinate tripodal ligand.

9. A process as claimed in claim 6 wherein any one of the group 13 metals, Al, Ga and In is complexed with the amine phosphinate tripodal ligand.

10. A process as claimed in claim 6 wherein any one of the lanthanide metals, La, Ce, Pr, Nd, Pm, Sm, Eu, Gd, Tb, Dy, Ho, Er, Tm, Yb and Lu, is complexed with the amine phosphinate tripodal ligand.

11. A process as claimed in claim 10 wherein the lanthanide metal is Sm or Ho.

12. A process as claimed in claim 8 wherein the rare earth is Sc or Y.

13. A process as claimed in claim 8 wherein the amine phosphinate tripodal ligand is of the formula:

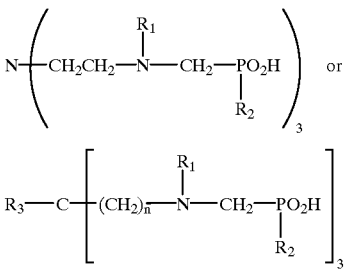

wherein n is 1 or 2, $R_1$ and $R_3$ are H, $CH_3$, $C_2H_5$ or other alkyl; and $R_2$ is $C_6H_5$, $CH_3$, $CH_2OH$, other alkyl, substituted alkyl, or aryl.

14. A process as claimed in claim 8 wherein the amine phosphinate tripodal ligand is:

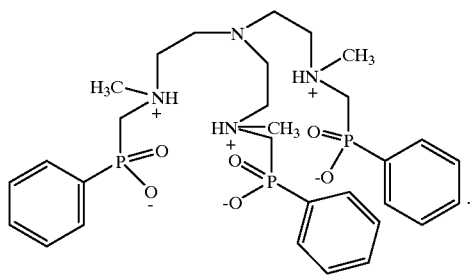
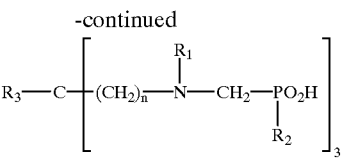

H₃ppma

15. A chelate comprising a metal ion and an amine phosphinate tripodal ligand of the formula:

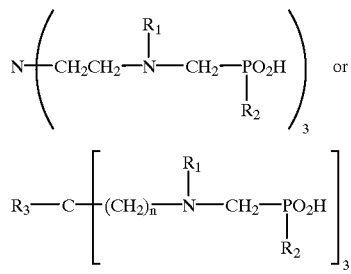

wherein n is 1 or 2, $R_1$ and $R_3$ are H, $CH_3$, $C_2H_5$ or other alkyl; and $R_2$ is $C_6H_5$, $CH_3$, $CH_2OH$, other alkyl, substituted alkyl, or aryl.

16. A chelate as claimed in claim 15 wherein the metal ion is selected from the group consisting of Tc, Re, the group 13 metals and the rare earths.

17. A chelate comprising a complex of a trivalent metal ion of the group 13 metals, Al, Ga and In, and the rare earths Sc, Y, La, Ce, Pr, Nd, Pm, Sm, Eu, Gd, Tb, Dy, Ho, Er, Tm, Yb and Lu and an amine phosphinate tripodal ligand of the formula:

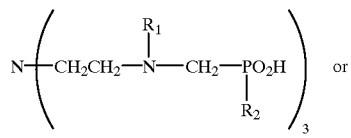

-continued $$R_3-C-\left[(CH_2)_n-\underset{R_2}{\overset{R_1}{N}}-CH_2-PO_2H\right]_3$$

wherein n is 1 or 2, $R_1$ and $R_3$ are H, $CH_3$, $C_2H_5$ or other alkyl; and $R_2$ is $C_6H_5$, $CH_3$, $CH_2OH$, other alkyl, substituted alkyl, or aryl.

18. A chelate as claimed in claim 17 wherein the complex is a group 13 metal complex and the metal is selected from the group consisting of Al, Ga and In.

19. A chelate as claimed in claim 17 wherein the complex is a lanthanide complex, and the lanthanide is selected from the group consisting of La, Ce, Pr, Nd, Pm, Sm, Eu, Gd, Tb, Dy, Ho, Er, Tm, Yb and Lu.

20. A chelate as claimed in claim 17 wherein the lanthanide metal is Sm or Ho.

21. A chelate as claimed in claim 17 wherein the amine phosphinate tripodal ligand is:

H₃ppma

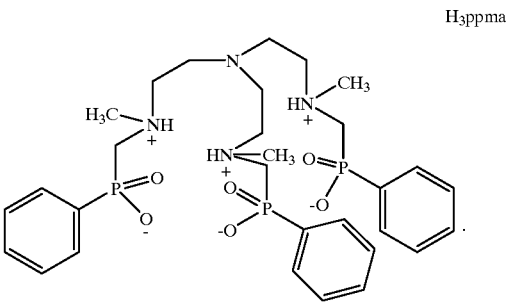

22. A chelate as claimed in claim 15 wherein the rare earth is Sc or Y.

* * * * *